(12) United States Patent
Kaneda et al.

(10) Patent No.: US 7,927,615 B2
(45) Date of Patent: Apr. 19, 2011

(54) THICKENER, COSMETIC PREPARATION CONTAINING THE SAME, AND PROCESS FOR PRODUCING THE SAME

(75) Inventors: Isamu Kaneda, Yokohama (JP); Toshio Yanaki, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 13 days.

(21) Appl. No.: 12/576,438

(22) Filed: Oct. 9, 2009

(65) Prior Publication Data

US 2010/0029787 A1 Feb. 4, 2010

Related U.S. Application Data

(62) Division of application No. 10/513,824, filed as application No. PCT/JP03/05863 on May 12, 2003, now abandoned.

(30) Foreign Application Priority Data

May 14, 2002 (JP) ................................. 2002-138533
Jul. 18, 2002 (JP) ................................. 2002-209587

(51) Int. Cl.
*A61K 8/81* (2006.01)
*A61K 8/04* (2006.01)
*A61Q 1/00* (2006.01)
*A61Q 15/00* (2006.01)
*A61Q 5/00* (2006.01)

(52) U.S. Cl. ........ 424/401; 514/844; 524/812; 524/814; 524/817; 524/831; 524/832

(58) Field of Classification Search .................. 424/401; 514/844; 524/812, 814, 817, 831, 832
See application file for complete search history.

(56) References Cited

U.S. PATENT DOCUMENTS 4,540,740 A * 9/1985 Olson et al. .................... 524/811
6,197,287 B1 * 3/2001 Mallo et al. ................. 424/70.16

* cited by examiner

*Primary Examiner* — Kelechi C Egwim
(74) *Attorney, Agent, or Firm* — Townsend & Banta

(57) ABSTRACT

The present invention is a thickener consisting of a microgel obtained by radical polymerization of water soluble ethylene-type unsaturated monomers dissolved in the dispersion phase in a composition having an organic solvent or an oil component as the dispersion medium and water as the dispersion phase, as well as a cosmetic containing said thickener.

Also, the present invention is a method of manufacturing a water-swelling polymer in a radical polymerization system consisting of a composition having an organic solvent or oil component as the dispersion medium and an aqueous solution of a water soluble ethylene type unsaturated monomer as the dispersion phase wherein said system contains a surfactant chosen in such a way that the aforementioned composition forms a single phase W/O microemulsion or fine W/O emulsion at a thermal radical polymerization temperature and said thermal radical polymerization is carried out at a temperature equal to or higher than the phase transition temperature of the radical polymerization system, yet not higher than the phase transition temperature by 20° C. or more.

16 Claims, 7 Drawing Sheets

THICKENER, COSMETIC PREPARATION CONTAINING THE SAME, AND PROCESS FOR PRODUCING THE SAME

CROSS REFERENCE TO A RELATED APPLICATIONS

This is a Divisional patent application of application Ser. No. 10/513,824, filed Nov. 9, 2004, now pending.

TECHNICAL FIELD

The present invention relates to a thickener consisting of a microgel, a method of manufacturing said thickener, and a cosmetic containing said thickener. More specifically, the present invention relates to a thickener consisting of a microgel that exhibits a superior thickening effect and gives superior sensation during use when blended in a cosmetic, a method of manufacturing said thickener, and a cosmetic containing said thickener.

The present invention is a method of manufacturing a water-swelling polymer in the form of a microgel that can be used as a water soluble thickener, and relates to the reverse phase microemulsion polymerization method using thermal radical polymerization.

The water-swelling polymer manufactured according to the present invention can be utilized for everyday articles such as cosmetics, medical drugs, and sanitary goods, as well as in civil engineering and agriculture.

BACKGROUND ART

Invention of Claims 1-14

Examples of water soluble thickeners that can be used in a wide range of applications including medical drugs and cosmetics include various polysaccharides, natural polymers such as gelatin, synthetic polymers such as polyoxyethylene and cross-linked poly(meth)acrylic acid, and inorganic minerals such as montmorillonite and silica.

Of these, the cross-linked poly(meth)acrylic acid in particular is frequently used as a water soluble thickener or stabilizer in medical drug and cosmetic industries, particularly in cosmetics, because it is inexpensive, has a high thickening effect, and gels with a small amount.

However, cross-linked poly(meth)acrylic acid exhibits an extreme reduction of the viscosity and loses the ability to gel in an acidic aqueous solution having a pH of 5 or lower and/or an aqueous solution under the presence of salt, due to suppression of the dissociation of carboxyl groups. Therefore, it cannot be used in recipes that require acidic conditions and/or the coexistence of salt.

In particular, this characteristic can be a fatal flaw for a thickener for cosmetics for which usability is an important factor. For example, the blend ratio would have to be increased substantially to maintain the thickening effect under acidic conditions of pH 5 or lower and/or in the presence of salts, resulting in substantially degraded usability. That is, when applied to the skin stickiness arises; this stickiness is a very serious problem in terms of the usability of the cosmetic.

In order to solve this problem, a copolymer of acrylamidealkylsulfonic acid and acrylic acid (Japanese Patent Laid-Open No. H9-157130 bulletin), a copolymer of acrylamidealkylsulfonic acid and unsaturated monomers containing alkyl groups (Japanese Patent Laid-Open No. H10-279636 bulletin), a homopolymer of 2-acrylamido-2-methylpropanesulfonic acid (Japanese Patent Laid-Open No. H10-67640 bulletin), etc. have been used in cosmetics.

The aforementioned polymer having the acrylamidealkylsulfonic acid skeleton has improved acid resistance and can be used in recipes requiring acidic conditions; however, it does not have satisfactory usability as a thickener for cosmetics because it causes stickiness when it is almost dry, probably caused by acrylic acid.

In view of the aforementioned situation, the inventors discovered that satisfactory usability can be achieved by adding, as a water soluble thickener, a copolymer obtained by copolymerizing 2-acrylamido-2-methylpropanesulfonic acid or its salt, dialkylacrylamide, and cross-linking monomers (Japanese Patent Laid-Open No. 2001-114641 bulletin) to a cosmetic.

The aforementioned copolymer is a polymer gel obtained by radical polymerization in a homogeneous polymerization system; after the polymer gel is manufactured, it is mechanically crushed and added to a cosmetic as a thickener powder. The polymer gel particles are large and sometimes cause a problem in terms of the external appearance of the cosmetic. Also, there is room for improvement in terms of the thickening effect.

On the other hand, the most widely used thickener for cosmetics today is a polymer of acrylic acid collectively called carboxyvinyl polymer; commercially available product names include Hiviswako (from Wako Pure Chemical Industries, ltd.), Syntalen (from 3V SIGMA company), and Carbopol (from Goodric company). These thickeners are chemically cross-linked polymers (The B.F. Goodrich Company, Specialty Polymers and Chemical Div., Carbopol Data Sheets and Applications Literature).

Such cross-linked polymers, dispersed in water, have a very high thickening effect, and are widely used as thickeners for cosmetics and livingware (for example, Barry, B W and Meyer M C Int. J. Pharm 2: 1 (1979)).

However, these carboxyvinyl polymers have a problem in that their thickening ability is only exhibited in a limited pH range. Carboxyvinyl polymers swell and thicken in water because carboxyl groups in the polymer dissociate. Therefore, carboxyvinyl polymers have a very serious shortcoming in that they do not function as a thickener in a weakly acidic or lower pH range where carboxyl groups are not dissociated sufficiently; the development of a thickener capable of thickening in a wider pH range to replace them is strongly desired today.

Furthermore, some cosmetic recipes have a high concentration of ethanol; thickening such recipes efficiently with a conventional thickener such as a carboxyvinyl polymer is a very difficult task.

In view of the aforementioned problem, the inventors conducted earnest research and amazingly discovered that a microgel consisting of a synthetic polymer electrolyte prepared by a specific reverse phase emulsification polymerization solves the aforementioned problems and exhibits an exceptional thickening effect and sensation during use, and thus completed the present invention.

The present invention uses a microgel consisting of a synthetic polymer electrolyte prepared by a specific reverse phase emulsion polymerization (reverse phase microemulsion polymerization) as a cosmetic thickener; its object is to provide a new type of thickener that overcomes the shortcomings of carboxyvinyl polymers and polymer gels consisting of synthetic polymer electrolytes prepared by the homogeneous polymerization method or reverse phase suspension polymerization method.

Invention of Claims 15-21

There have been several scientific papers reporting methods of manufacturing polymers in which water soluble monomers are polymerized by means of the reverse phase emulsion polymerization method {for example, F. Candau et al. J. Colloid and Interface Science, 101(1) 167 (1984), J. Barton. Polymer International, 30 151 (1993), J. Hernabdez-Barajas et al. Polymer. 38 5623 (1997)}.

However, these reports are about W/O emulsion systems wherein an excessive amount of surfactants are added; they are not suitable for industrial manufacturing of polymers.

Industrial application examples include Japanese Patent Laid-Open No. H9-12613 bulletin that discloses a method to use the reverse phase emulsion polymerization method to manufacture water-absorbing microgel particles and make them into a certain size so they are suitable for diapers and menstrual sanitary products. Also, Japanese Patent No. 1911623 discloses a method of manufacturing a thickener by means of reverse phase emulsion polymerization using acrylic acid.

In these reverse phase emulsion polymerization methods, however, the particle size in the water phase, where the polymerization occurs, is not controlled, and as a result the obtained microgel water-swelling polymer has a low effect as a thickener, not suitable for practical use.

Based on the aforementioned view point, the inventors conducted earnest research and completed the present invention by discovering that desirable microgel-like water-swelling polymers can be manufactured with reverse phase emulsion polymerization by choosing the polymerization temperature and the surfactant in such a way that the polymerization system is a single phase W/O microemulsion or fine W/O emulsion, which enables a nanometer order control of the particle size of the water phase, which is the dispersion phase.

DISCLOSURE OF INVENTION

Invention of Claims 1-14

That is, the present invention provides a thickener consisting of a microgel obtained by radical polymerization of water soluble ethylene-type unsaturated monomers dissolved in the dispersion phase in a composition having an organic solvent or an oil component as the dispersion medium and water as the dispersion phase.

Also, the present invention provides a thickener consisting of a microgel obtained by radical polymerization of water soluble ethylene-type unsaturated monomers dissolved in the dispersion phase in a composition having an organic solvent or an oil component as the dispersion medium and water as the dispersion phase wherein said composition contains a surfactant and forms a single phase microemulsion or fine W/O emulsion.

Furthermore, the present invention provides a thickener consisting of said microgel wherein the apparent viscosity of the microgel aqueous dispersion having 0.5% (mass percentage) of it at 25° C. is 10,000 mPa·s or higher at a shear rate of $1.0\ s^{-1}$.

Also, the present invention provides a thickener consisting of said microgel wherein the apparent viscosity of the microgel ethanol dispersion having 0.5% (mass percentage) of it at 25° C. is 5,000 mPa·s or higher at a shear rate of $1.0\ s^{-1}$.

Furthermore, the present invention provides a thickener consisting of said microgel wherein the dynamic elastic modulus of the microgel aqueous or ethanol dispersion having 0.5% (mass percentage) of it at 25° C. satisfies a relationship G' (stored elastic modulus)>G" (loss elastic modulus) at a strain of 1% or less and a frequency range of 0.01-10 Hz.

Also, the present invention provides the aforementioned thickener wherein said water soluble ethylene-type unsaturated monomer is an ionic acrylamide derivative and dialkylacrylamide represented by general formula (1).

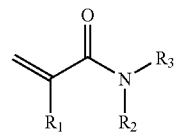

General formula (1)

($R_1$ denotes a H or methyl group; $R_2$ and $R_3$, independent of each other, denote a methyl, ethyl, propyl, or isopropyl group.)

Also, the present invention provides the aforementioned thickener wherein said water soluble ethylene-type unsaturated monomer is a dialkylacrylamide represented by general formula (1) and an anionic acrylamide derivative represented by general formula (2).

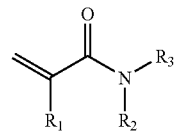

General formula (1)

($R_1$ denotes a H or methyl group; $R_2$ and $R_3$, independent of each other, denote a methyl, ethyl, propyl, or isopropyl group.)

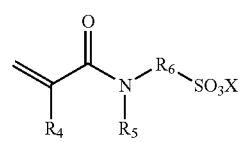

General formula (2)

($R_4$ and $R_5$, independent of each other, denote a H or methyl group, $R_6$ denotes a straight chain or branched alkyl group having 1-6 carbon atoms, and X denotes a metal ion or $NH_3$.)

Furthermore, the present invention provides the aforementioned thickener wherein said water soluble ethylene-type unsaturated monomer is a dialkylacrylamide represented by general formula (1) and a cationic acrylamide derivative represented by general formula (3).

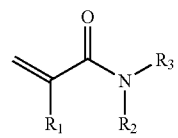

General formula (1)

($R_1$ denotes a H or methyl group; $R_2$ and $R_3$, independent of each other, denote a methyl, ethyl, propyl, or isopropyl group.)

General formula (3)

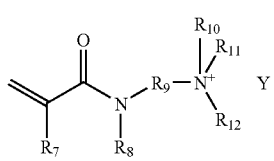

($R_7$ denotes a H or methyl group, $R_8$ denotes a H or straight chain or branched alkyl group having 1-6 carbon atoms, $R_9$ denotes a straight chain or branched alkyl group having 1-6 carbon atoms, $R_{10}$, $R_{11}$, and $R_{12}$ denote a methyl group or ethyl group, and Y denotes a metal ion.)

Furthermore, the present invention provides the aforementioned thickener wherein said water soluble ethylene-type unsaturated monomer is a dialkylacrylamide represented by general formula (1), an anionic acrylamide derivative represented by general formula (2), and a cross-linking monomer represented by general formula (4).

General formula (1)

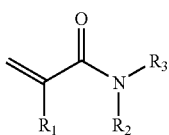

($R_1$ denotes a H or methyl group; $R_2$ and $R_3$, independent of each other, denote a methyl, ethyl, propyl, or isopropyl group.)

General formula (2)

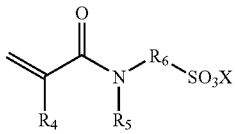

($R_4$ and $R_5$, independent of each other, denote a H or methyl group, $R_6$ denotes a straight chain or branched alkyl group having 1-6 carbon atoms, and X denotes a metal ion or $NH_3$.)

General formula (4)

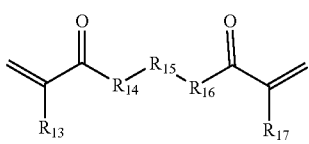

{ $R_{13}$ and $R_{17}$ denote a H or methyl group;
$R_{14}$ and $R_{16}$ denote —O— or —NH—;
$R_{15}$ denotes a straight chain or branched alkyl group having 1-6 carbon atoms or
—(CH$_2$CH$_2$O)$_n$—
(n = 4-100). }

Also, the present invention provides the aforementioned thickener wherein said water soluble ethylene-type unsaturated monomer is a dialkylacrylamide represented by general formula (1), a cationic acrylamide derivative represented by general formula (3), and a cross-linking monomer represented by general formula (4).

General formula (1)

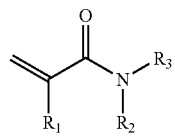

($R_7$ denotes a H or methyl group; $R_2$ and $R_3$, independent of each other, denote a methyl, ethyl, propyl, or isopropyl group.)

General formula (3)

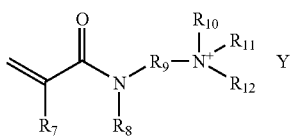

($R_7$ denotes a H or methyl group, $R_8$ denotes a H or straight chain or branched alkyl group having 1-6 carbon atoms, $R_9$ denotes a straight chain or branched alkyl group having 1-6 carbon atoms, $R_{10}$, $R_{11}$, and $R_{12}$ denote a methyl group or ethyl group, and Y denotes a metal ion.)

General formula (4)

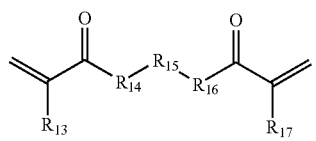

{ $R_{13}$ and $R_{17}$ denote a H or methyl group;
$R_{14}$ and $R_{16}$ denote —O— or —NH—;
$R_{15}$ denotes a straight chain or branched alkyl group having 1-6 carbon atoms or
—(CH$_2$CH$_2$O)$_n$—
(n = 4-100). }

Furthermore, the present invention provides a method of manufacturing the aforementioned thickener comprising radical polymerization of water soluble ethylene-type unsaturated monomers dissolved in the dispersion phase in a composition having an organic solvent or an oil component as the dispersion medium and water as the dispersion phase.

Also, the present invention provides a cosmetic containing the aforementioned thickener.

Furthermore, the present invention provides a skin treatment composition containing the aforementioned thickener and a medically acceptable carrier.

In addition, the present invention provides a cosmetic containing the aforementioned thickener and a cosmetically acceptable carrier.

Invention of Claims 15-21

That is, the present invention provides a method of manufacturing a water-swelling polymer in a radical polymerization system consisting of a composition having an organic solvent or oil component as the dispersion medium and an aqueous solution of a water soluble ethylene type unsaturated monomer as the dispersion phase wherein said system contains a surfactant chosen in such a way that the aforementioned composition forms a single phase W/O microemulsion or fine W/O emulsion at a thermal radical polymerization temperature and said thermal radical polymerization is carried out at a temperature equal to or higher than the phase transition temperature of the radical polymerization system, yet not higher than the phase transition temperature by 20° C. or more.

Also, the present invention provides the aforementioned method of manufacturing the water-swelling polymer wherein the aforementioned surfactant is a nonionic surfactant.

Furthermore, the present invention provides the method of manufacturing the aforementioned water-swelling polymer wherein the mass ratio between the water phase and the surfactant is water phase/surfactant=0.5-20 in the aforementioned radical polymerization system.

Also, the present invention provides the aforementioned method of manufacturing the aforementioned water-swelling polymer wherein the concentration of the surfactant is 1 mass % or more and 30 mass % or less in the aforementioned radical polymerization system.

Furthermore, the present invention provides the method of manufacturing the aforementioned water-swelling polymer wherein the apparent viscosity of the microgel aqueous dispersion having 0.5% of the aforementioned water-swelling polymer at 25° C. is 10,000 mPa·s or higher at a shear rate of $1.0\ s^{-1}$.

Also, the present invention provides the aforementioned method of manufacturing the aforementioned water-swelling polymer wherein the dynamic elastic modulus of the water dispersion having 0.5% (mass percentage) of the aforementioned water-swelling polymer at 25° C. satisfies the relationship G' (stored elastic modulus)>G" (loss elastic modulus) at a strain of 1% or less and a frequency range of 0.01-10 Hz.

Furthermore, the present invention provides the aforementioned method of manufacturing the aforementioned water-swelling polymer wherein said water soluble ethylene-type unsaturated monomer is a dimethylacrylamide and 2-acrylamido-2-methylpropanesulfonic acid.

BEST MODE FOR CARRYING OUT THE INVENTION

Figure 1:
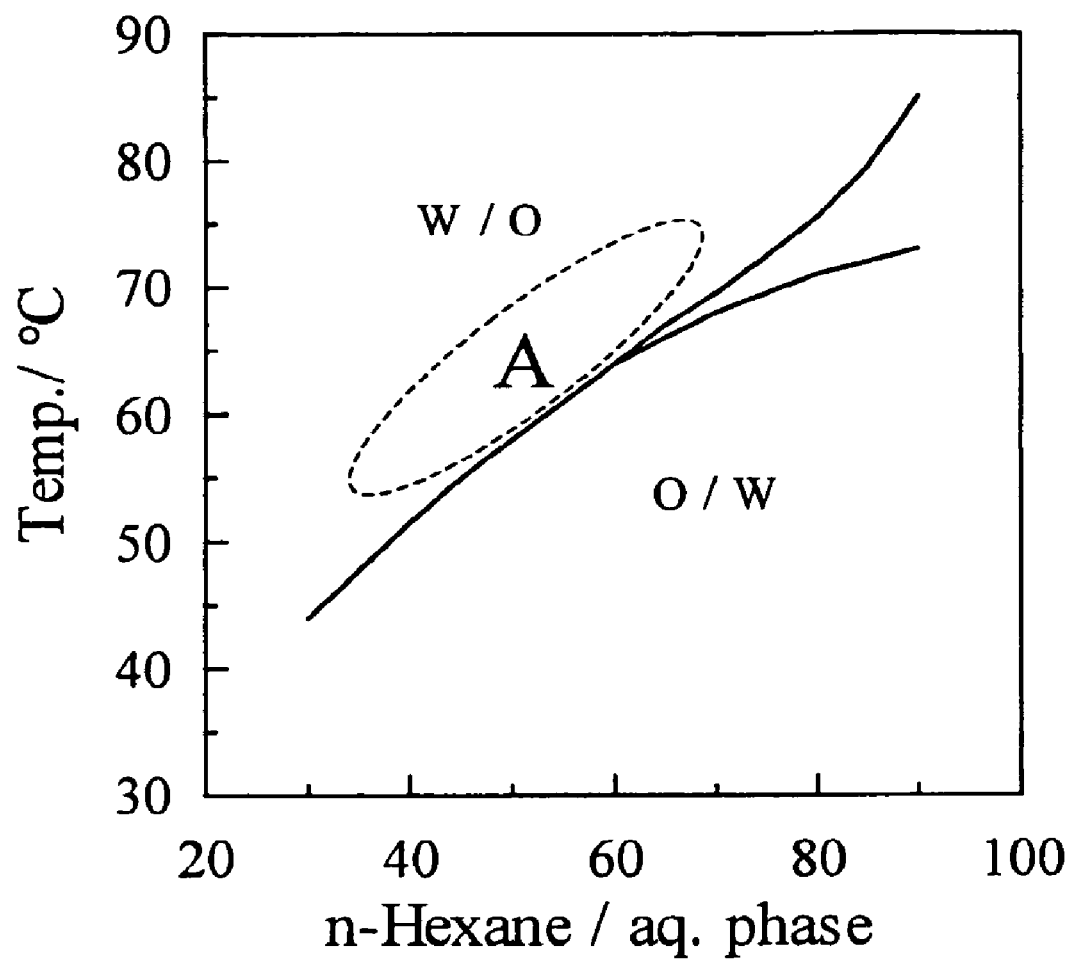
FIG. 1 is a 3 component system phase diagram of hexane (shown as W)/surfactant/water soluble ethylene monomer aqueous solution (shown as 0).
Figure 2:
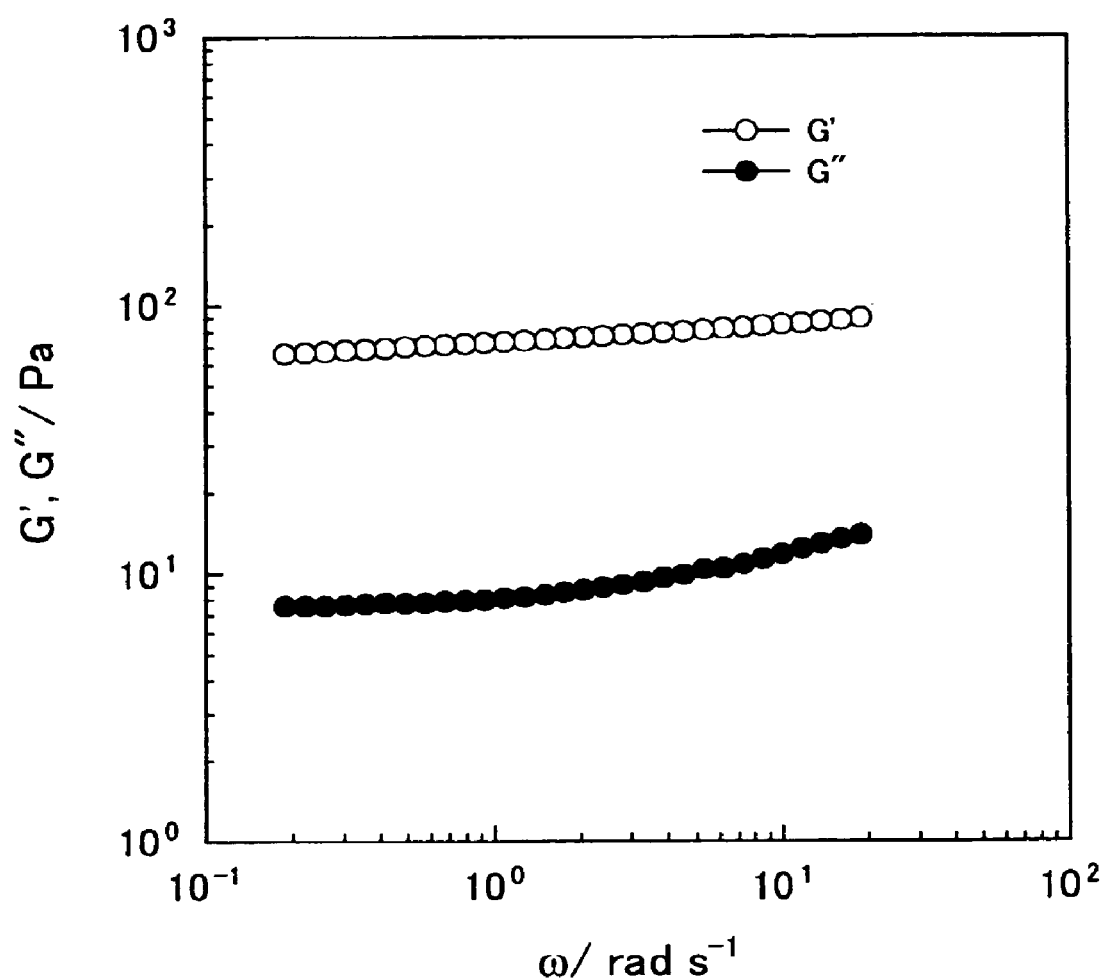
FIG. 2 is a graph showing the dynamic elastic modulus of water.

The present invention is described in detail below.

Invention of Claims 1-14

A thickener consisting of a microgel is a thickener consisting of a synthetic polymer microgel obtained by radical polymerization of water soluble ethylene-type unsaturated monomers dissolved in the dispersion phase in a composition having an organic solvent or an oil component as the dispersion medium and water as the dispersion phase.

That is, a polymer microgel manufactured by the polymerization method generally called the reverse emulsion polymerization method is used for a thickener; its polymerization method and mechanical properties are different from those of a thickener consisting of a synthetic polymer obtained by a homogeneous polymerization system disclosed in, for example, Japanese Patent Laid-Open No. 2001-114641 bulletin.

A microgel is synthetic polymer electrolyte fine particles manufactured by means of the reverse phase microemulsion polymerization method. The thickener consisting of the microgel of the present invention swells in water, ethanol, or a water/ethanol mixed solution to provide a highly viscous solution that appears homogeneous to the naked eye.

The method of manufacturing a thickener of the present invention, i.e. the polymerization system for the microgel used for the thickener, is different from the homogeneous polymerization system used to manufacture the synthetic polymer used as a conventional thickener.

The synthetic polymer from the homogeneous polymerization system disclosed in Japanese Patent Laid-Open No. 2001-114641 bulletin is not the microgel used in the present invention; this synthetic polymer has to be crushed to powder after polymerization before being added to a cosmetic. Also, the synthetic polymer gel stands out and may cause an appearance problem.

In contrast, the microgel used in the present invention is polymerized in an inhomogeneous polymerization system. The obtained synthetic polymer is a fine polymer gel, or microgel; it does not have to be crushed into powder before being added to a cosmetic, it exhibits a superior thickening effect and a superior sensation during use, and it gives a good appearance to the cosmetic.

An example of the reverse phase emulsion polymerization method for polymers, described in Japanese Patent No. 1911623 bulletin, manufactures a water-swelling polymer using acrylic acid by means of reverse phase polymerization and uses it as a thickener; this, however, is different from the microgel used in the present invention that improves the shortcomings of carboxyvinyl polymers widely used today.

Japanese Patent Laid-Open No. H9-12613 bulletin discloses a method to use the reverse phase emulsion polymerization method to manufacture water-absorbing microgel particles and make them into a certain size so they are suitable for diapers and menstrual sanitary products; this technology, however, cannot be used for cosmetic thickeners and is completely different from the microgel used in the present invention.

The thickener of the present invention is manufactured with the reverse phase emulsion polymerization method. That is, this thickener is manufactured by radical polymerization of water soluble ethylene-type unsaturated monomers dissolved in the dispersion phase in a composition having an organic solvent or an oil component as the dispersion medium and water as the dispersion phase. The polymerized microgel is rinsed and dried, but there is no need for crushing.

It is preferable to manufacture the thickener consisting of a microgel by using a surfactant whose hydrophilicity/lipophilicity balance (HLB) is specifically selected so that the reverse emulsion polymerization system forms a single phase microemulsion or fine W/O emulsion.

A single phase microemulsion is a state wherein the oil phase and water phase coexist in a thermodynamically stable manner and the surface tension between the oil and water is at a minimum. A fine W/O emulsion is a state wherein the oil and water exist as a fine W/O emulsion in a thermodynamically unstable but kinetically stable fashion. Generally, the particle size of the inner water phase of a fine W/O emulsion is several tens to 100 nm. These states are determined solely by the system composition and temperature, and are not affected by mechanical stirring conditions and such.

The composition that makes up the polymerization system consists of the dispersion medium (outer phase) consisting of an organic solvent or oil component that does not mix with water and the dispersion phase (inner phase) consisting of water.

Examples of the preferable organic solvent include alkanes such as pentane, hexane, heptane, octane, nonane, decane, and undecane; cycloalkanes such as cyclopentane, cyclohexane, cycloheptane, and cyclooctane; and aromatic and cyclic hydrocarbons such as benzene, toluene, xylene, decaline, and naphthalene.

Examples of the preferable oil component include nonpolar oil components such as paraffin.

The water soluble ethylene type unsaturated monomer is dissolved in water, which is the dispersion phase, and then mixed with the organic solvent or oil component, which is the dispersion medium; after the temperature is raised to the prescribed temperature, the polymerization initiator is added to the water phase to carry out the polymerization.

In the inhomogeneous polymerization method, physical properties of the manufactured polymer are known to be different depending on the stirring conditions during the polymerization. That is because the emulsion system is thermodynamically unstable and therefore the shape and size of the emulsion particles change depending on the stirring conditions. In the present invention, the inventors discovered that these problems can be avoided by carrying out the polymerization in the thermodynamically stable single microemulsion region or the metastable fine W/O emulsion region near the single phase region. Specifically, a microgel having a high thickening effect has become possible by polymerizing the polymer in a fine water phase (water drops) by adjusting the composition of the polymerization system (type of the organic solvent, HLB of the surfactant) in such a way that the aforementioned single phase microemulsion or fine W/O emulsion region appears near the optimum polymerization temperature for the polymerization initiator for a conventional thermal polymerization or redox polymerization.

An example is shown in FIG. 1 in the form of a phase diagram. FIG. 1 is a 3 component system phase diagram of hexane (shown as W)/surfactant/water soluble ethylene monomer aqueous solution (shown as 0); hexane is used for the organic solvent. The A region shown in FIG. 1 is the single phase microemulsion region/fine W/O emulsion region; a preferable microgel can be polymerized by carrying out the polymerization in this region.

On the contrary, in the case of the polymer thickener from a conventional suspension polymerization (for example, the method described in Japanese Patent Laid-Open No. 2001-1146641) bulletin, the particle size of water drops during polymerization is difficult to control and a microgel of good quality is difficult to obtain.

For the water soluble ethylene type unsaturated monomer, joint use of a nonionic monomer and ionic monomer (anionic monomer or cationic monomer) is preferable.

For the nonionic monomer, the dialkylacrylamide represented by the aforementioned general formula (1) is preferable.

For the ionic monomer, the anionic acrylamide derivative represented by general formula (2) or the cationic acrylamide derivative represented by general formula (3) is preferable.

A particularly preferable dialkylacrylamide is dimethylacrylamide and di-ethylacrylamide.

Particularly preferable ionic acrylamide derivatives are 2-acrylamido-2-methylpropanesulfonic acid and its salts.

A particularly preferable cationic acrylamide derivative is N,N-dimethylaminopropylacrylamidemethyl chloride.

The monomer composition ratio of the nonionic monomer and the ionic monomer in the polymerization system (feed ratio of the polymerization system) is selected based on the monomer composition ratio of the target microgel. The monomer composition ratio of the microgel and the feed ratio into the polymerization system are about the same. The feed ratio of the nonionic monomer and the ionic monomer in the polymerization system (molar ratio) for copolymerization is usually in the range of Nonionic monomer:Ionic monomer=0.5:9.5 to 5:0.5, preferably 1:9 to 9:1, more preferably 7:3 to 9:1. The optimum ratio is Nonionic monomer:Ionic monomer=8:2.

The aforementioned water soluble ethylene type unsaturated monomer is then chosen at will and the thickener of the present invention is polymerized. A particularly preferable thickener is a dipolymer microgel copolymerized from monomers of dimethylacrylamide and 2-acrylamido-2-methylpropanesulfonic acid, used as the water soluble ethylene type unsaturated monomer. In this case, without requiring a cross-linking monomer, a thickener that exhibits a superior thickening effect and sensation during use can be obtained by self cross-linking. A cross-linking monomer can be used; a cross-linking monomer represented by general formula (4) is preferable, and methylenebisacrylamide is particularly preferable.

In order to dissolve the water soluble ethylene type unsaturated monomer in the dispersion phase and polymerize a microgel preferable for the present invention, it is necessary to select the optimum outer phase oil component or organic solvent and the optimum surfactant. The inventors discovered that a microgel having preferable rheological properties as a thickener can be obtained by creating a condition wherein a single phase microemulsion or fine W/O emulsion is formed at an usual thermal radical polymerization temperature by preparing a phase diagram and thus choosing the polymerization system composition in such a way that the clouding point is at the temperature suitable for the thermal radical polymerization.

Preferable surfactants include polyoxyethylenecetyl ether, polyoxyethyleneoleyl ether, polyoxyethylenestearyl ether, polyoxyethylenenonylphenyl ether, polyoxyethylenelauryl ether, polyoxyethylenehexyldecyl ether, polyoxyethyleneisostearyl ether, polyoxyethyleneoctyldodecyl ether, polyoxyethylenebehenyl ether, polyoxyethylenecholesteryl ether, polyoxyethylene hydrogenated castor oil, sorbitan fatty acid ester, mono-fatty acid glycerin, tri-fatty acid glycerin, polyglycerin fatty acid ester, polyoxyethyleneglycerin isostearate, polyoxyethyleneglycerin monostearate, polyoxyethyleneglyceryl distearate, and polyoxyethyleneglyceryl tristearate.

These surfactants can be combined to adjust the HLB to the desired level and then added to the polymerization system.

In the case of the microgel obtained by copolymerizing a dialkylacrylamide and an acrylamide type ionic monomer, a spontaneous cross-linking reaction develops and a chemically self-cross-linked microgel can be obtained without having to copolymerize with a multifunctional cross-linking monomer as a third ingredient, thus providing a particularly preferable thickener for the present invention.

Although the third ingredient, the multifunctional cross-linking monomer, is not required, the microgel used in the present invention can still be synthesized if such a monomer is added for copolymerization. For the multifunctional cross-linking monomer, the monomers represented by general formula (4) are preferable; one, two, or more of the monomers represented by general formula (4) can be used for cross-linking. It is essential that these cross-linking monomers can effectively have a cross-linking structure in the polymerization system of the dialkylacrylamide and the ionic acrylamide derivative.

Examples of the cross-linking monomer include ethylene glycol diacrylate, ethylene glycol dimethacrylate, polyoxyethylene diacrylate, polyoxyethylene dimethacrylate, diethylene glycol dimethacrylate, trimethylolpropane triacrylate, N,N'-methylenebisacrylamide, N,N'-ethylenebisacrylamide, triallyl cyanurate, and pentaerythrithol dimethacrylate; one, two, or more chosen from these can be used. In the present invention, N,N'-methylenebisacrylamide is particularly preferable to use.

In the copolymer that is the thickener of the present invention, the content molar ratio of the 2-acrylamido-2-methylpropanesulfonic acid unit and the dialkylacrylamide unit is usually 2-acrylamido-2-methylpropanesulfonic acid unit dialkylacrylamide unit=0.5:9.5 to 9.5:0.5, preferably 1:9 to 9:1, and more preferably 3:7 to 1:9. The optimum ratio is 2-acrylamido-2-methylpropanesulfonic acid unit:dialkylacrylamide unit=2:8. The viscosity of the thickener of the present invention results from the extension of the molecular chains due to the electrostatic repulsion of the sulfonyl group, which is a strongly dissociating group, and the spontaneous cross-linking reaction of dialkylacrylamide or the cross-linked structure formed by the cross-linking monomer; if the content of the 2-acrylamido-2-methylpropanesulfonic acid unit or its salt is less than 5 mole % compared with the dialkylacrylamide unit, then a sufficient viscosity may not be obtained because a sufficient extension of the molecular chains does not occur.

The blend ratio of the cross-linking monomer is preferably 0.0001-2.0 mole % of the total moles of the 2-acrylamido-2-methylpropanesulfonic acid or its salt and the dialkylacrylamide. If it is less than 0.0001 mole %, then the obtained thickener may not exhibit the effect of cross-linking. If more than 2 mole % is used for preparation, a sufficient thickening effect may not be achieved because the cross-link density is too high and the microgel cannot swell enough.

The weight average molecular weight of the microgel used in the present invention is 100,000-5,000,000 (PEG equivalent, measured with the GPC); it is adjusted according to the desired viscosity of the thickener.

The microgel obtained by the aforementioned polymerization method has all the rheological properties listed in (1)-(3) below. A thickener consisting of this microgel is obtained by the manufacturing method according to the aforementioned polymerization method and used preferably as a thickener.

(1) The apparent viscosity of the microgel aqueous dispersion having 0.5% (mass percentage) of the microgel in water is 10,000 mPa·s or higher at a shear rate of $1.0 \text{ s}^{-1}$.

(2) The apparent viscosity of the microgel ethanol dispersion having 0.5% (mass percentage) of the microgel is 5,000 mPa·s or higher at a shear rate of $1.0 \text{ s}^{-1}$.

(3) The dynamic elastic modulus of the microgel aqueous or ethanol dispersion having 0.5% (mass percentage) of it satisfies the relationship G'>G" at a strain of 1% or less and a frequency range of 0.01-10 Hz.

The apparent viscosity of the ethanol or water dispersion having the microgel is the viscosity measured with a cone/plate rheometer (MCR-300 from Paar Rhysica) at 25° C. and a shear rate of $1 \text{ s}^{-1}$.

The dynamic elastic modulus here refers to the stored elastic modulus (G') and the loss elastic modulus (G") measured at a strain of 1% or less and a frequency range of 0.01-10 Hz with the aforementioned measurement apparatus at a temperature of 25° C.

Following the polymerization, the microgel to be used in the present invention can be isolated in a powder form after a precipitation/purification process. The microgel thus isolated in a powder form is easily dispersed in water, ethanol, or a water/ethanol mixed solvent and quickly swells and functions as a thickener.

Also, by choosing a strongly acidic monomer (a monomer containing a sulfonic acid residue, for example) for the ionic monomer to be copolymerized into the microgel, even an acidic formulation can be thickened, which was not possible with conventional carboxyvinyl polymers.

Furthermore, the microgel used in the present invention can thicken or gel alcohol, which conventionally was considered difficult. The thickener of the present invention is used in thickening or gelling applications; when blended into a cosmetic as a thickener, it manifests a superior thickening effect and significantly reduces sliminess at the time of application of the cosmetic and stickiness when it is almost dried, making it possible to manufacture a cosmetic giving an exceptional sensation during use.

The cosmetic of the present invention is prepared by blending the aforementioned microgel as a thickener into the cosmetic base agent. The blend ratio of the thickener is determined according to the target cosmetic; there is no particular limitation. From the usability point of view, a preferable blend ratio is 0.01-10% (mass percentage), and more preferably 0.1-5% (mass percentage).

Furthermore, depending on the formulation of the cosmetic, oil based base agents, surfactants, powders, humectants, ultraviolet absorbents, alcohols, chelating agents, pH adjusting agents, preservatives, antioxidants, thickeners, drugs, dyes, pigments, perfumes, and water can be added within the range that does not affect the effect of the invention; and the cosmetic can be manufactured using a conventional method.

The type and preparation method of the cosmetic of the present invention are not limited in particular. It can be used in foundation cosmetics, makeup cosmetics, facial pack cosmetics, hair cosmetics, etc. The thickener of the present invention can be swollen in water or ethanol to manufacture a water- or ethanol-based base agent, preferably for lotions, beauty care liquids, hair dyes, etc. Also, an emulsified cosmetic can be prepared by means of mixing and stirring with an oil-based base agent.

The cosmetic of the present invention exhibits a stable thickening effect, and does not have the external appearance problem that is caused by a thickener consisting of a conventional polymer gel.

Invention of Claims 15-21

The manufacturing method of the present invention is a manufacturing method characterized by carrying out radical polymerization while controlling the droplet size of the water soluble monomer aqueous solution, which is the dispersion phase, by setting the polymerization temperature range higher or equal to the phase transition temperature of the polymerization system but no higher than 20° C. above the phase transition temperature, where the reverse phase polymerization system forms the W/O microemulsion or the fine W/O emulsion, by using a surfactant whose hydrophilicity/lipophilicity balance is appropriately selected.

In the present invention, the phase transition temperature refers to the temperature at which the continuous phase of the polymerization system changes from O/W to W/O. "The polymerization temperature range higher or equal to the transition temperature of the polymerization system but no higher than the transition temperature by more than 20° C." means that, assuming the phase transition temperature is X° C., the polymerization temperature is equal to or higher than X° C. and equal to or lower than (X+20)° C.

The single phase W/O microemulsion is a state in which the oil phase and the water phase coexist in a thermodynamically stable manner; in this state the oil phase is the continuous phase and water-swelling surfactant micelles are dispersed. The fine W/O emulsion is a phase that occurs in the vicinity of the aforementioned single phase W/O emulsion region; although this is a thermodynamically unstable state, the oil phase and the water phase exist as a W/O emulsion in a kinetically stable manner. In general, the particle size in the water phase of the single phase W/O emulsion and the fine W/O emulsion is approximately 10 to several hundred nm. Since the single phase W/O emulsion is in a thermodynamic equilibrium, its state is determined solely by the system composition and temperature, not affected by mechanical stirring conditions. The fine W/O emulsion, which occurs near the upper part of the single phase W/O emulsion formation temperature, forms fine W/O with a size of about several tens to several hundred nm even under usual stirring conditions. This means it is a very advantageous manufacturing method for industrial scaling up.

In the three component system of "oil phase (dispersion medium consisting of an organic solvent or oil component)/surfactant/water phase (monomer aqueous solution)" in the radical polymerization system, the size of the formed particles (water-swelling surfactant micelles or water droplets) depends on the quantity ratio of water phase/surfactant and the particle system becomes smaller as this ratio becomes smaller. Therefore, as the quantity ratio becomes smaller (more surfactant), finer particles can be formed; however, since the amount of the surfactant would increase, it is not suitable for industrial manufacturing. As a result, the mass ratio of the amounts of the water phase and the surfactant in the radical polymerization system of the present invention, i.e. water phase/surfactant, is preferably 0.5 or more and 20 or less. The amount of the water phase refers to the amount of the monomer aqueous solution consisting of water and the water soluble ethylene type unsaturated monomer. If a water soluble compound (such as a polymerization initiator) is added to the radical polymerization system, then the amount of the compound is also included.

The mass ratio of water and the water soluble ethylene type unsaturated monomer is chosen appropriately; the content of the water soluble ethylene type unsaturated monomer is preferably 10-40 mass %, more preferably 10-30 mass % of the entire water phase.

The total amount of the surfactant contained in the radical polymerization system is preferably 1 mass % or more and 30 mass % or less of the total amount of the composition constituting the radical polymerization system. If the total amount of the surfactant is less than 1 mass %, then the critical micelle formation concentration may be not reached in the oil phase and the single phase W/O emulsion may not be formed. 30 mass % or more would be unsuitable for industrial production.

The mass ratio of the water phase and the oil phase is preferably Water phase:Oil phase=1:9 to 6:4.

In the manufacturing method of the present invention, examples of the preferable organic solvent for the dispersion medium of the oil phase include alkanes such as pentane, hexane, heptane, octane, nonane, decane, and undecane; cycloalkanes such as cyclopentane, cyclohexane, cycloheptane, and cyclooctane; and aromatic and cyclic hydrocarbons such as benzene, toluene, xylene, decaline, and naphthalene. Examples of the preferable oil component for the dispersion medium include non-polar oil components such as paraffin.

These dispersion media are chosen based on the type of the water soluble ethylene type unsaturated monomer and the desired phase transition temperature.

The selection of the surfactant suitable for the present invention can be made essentially by measuring the phase transition temperature. The phase transition temperature is the temperature at which the continuous phase switches from O/W to W/O, i.e. the temperature at which the transition from the water phase continuous phase to the oil phase continuous phase occurs. In the manufacturing method of the present invention, this phase transition temperature is determined as a temperature at which the electrical conductivity, measured with a commercial circuit tester, suddenly drops practically to zero as the desired polymerization system is stirred and its temperature is raised.

The optimum type and amount of the surfactant is chosen in such a way that the phase transition temperature is equal to the thermal radical polymerization temperature. The thermal radical polymerization temperature is chosen based on the types of the water soluble ethylene type unsaturated monomer and the oil phase; a preferable temperature is about 30-100° C.; in the polymerization process, the thermal radical polymerization temperature can easily be adjusted to fit in the temperature range of the phase transition temperature up to 20° C. above this temperature.

Figure 6:
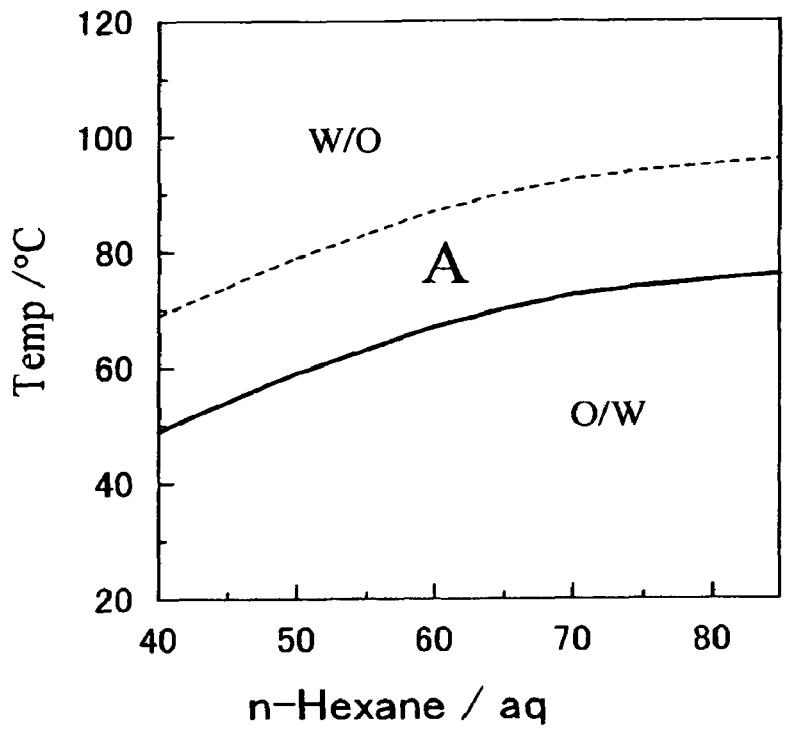
FIG. 6 is a phase diagram of the polymerization system composition consisting of 3 components, i.e. hexane (O)/surfactant/water soluble ethylene monomer aqueous solution (W).

An example of the phase transition temperature measurement is shown in FIG. 6. FIG. 6 shows an example of a pseudo three component polymerization system of hexane/polyoxyethylene (6) oleyl ether/water soluble ethylene type unsaturated monomer aqueous solution. In this polymerization system, a 80:20 molar ratio mixture of dimethylacrylamide and 2-acrylamido-2-methylpropanesulfonic acid dissolved in ion-exchanged water (20 mass %) is used for the water soluble ethylene type unsaturated monomer aqueous solution. This water soluble ethylene type unsaturated monomer aqueous solution and hexane were mixed to prepare mixtures having a mixing ratio (mass ratio) ranging from 10:90 to 40:60; sample solutions were prepared by adding polyoxyethylene (6) oleyl ether, 5 mass % of the total mixture, to each of the mixtures. The phase transition temperatures of the samples with different mixing ratios of the water soluble ethylene type unsaturated monomer aqueous solution and hexane were determined by using the system's electric conductivity as the indicator. In FIG. 6, the X axis shows the mixing ratio of the water soluble ethylene type unsaturated monomer aqueous solution and hexane (for example, if the value of n-Hexane/aq on the X axis is 70, 70 mass parts is hexane and the rest, 30 mass parts, is the water soluble ethylene type unsaturated monomer aqueous solution, i.e. the mass ratio of the hexane and the water soluble ethylene type unsaturated monomer aqueous solution is 70:30), and the Y axis shows the temperature (Celsius). The solid line in this figure connects the phase transition temperature of the samples; it is a so called solubilization limit curve. The dotted line connects the points above the aforementioned phase transition temperatures by +20° C. The region A, delineated by the solid line and dotted line, is the region where the single phase W/O emulsion-fine W/O emulsion occurs.

In the present invention, a water-swelling polymer in a fine microgel form can be manufactured at an optimum temperature range (phase transition temperature+20° C.) by selecting the dispersion medium and the water soluble ethylene type unsaturated monomer when preparing the polymerization system and selecting the surfactant in such a way that this system's phase transition temperature is equal to the thermal radical polymerization temperature (30-100° C.). The radical polymerization can be carried out using a prior art radical polymerization initiator and a prior art method, as long as the polymerization is carried out in region A. A photo polymerization initiator can be used as well, but is not suitable for industrial mass production.

In the manufacturing method of the present invention, a preferable surfactant is a nonionic surfactant for which the temperature dependence of the phase transition is strong. There is no limitation on the choice of the chemical species; one or a combination of two or more surfactants suitable for the polymerization system composition is chosen by actually measuring the electric conductivity in the desired polymerization system composition and/or by preparing a phase diagram of the three component system, i.e. the dispersion medium/surfactant/water soluble ethylene type unsaturated monomer.

Specific examples of the preferable surfactants include polyoxyethylenecetyl ether, polyoxyethyleneoleyl ether, polyoxyethylenestearyl ether, polyoxyethylenenonylphenyl ether, polyoxyethylenelauryl ether, polyoxyethylenehexyldecyl ether, polyoxyethyleneisostearyl ether, polyoxyethyleneoctyldodecyl ether, polyoxyethylenebehenyl ether, polyoxyethylenecholesteryl ether, polyoxyethylene hydrogenated castor oil, sorbitan fatty acid ester, mono-fatty acid glycerin, tri-fatty acid glycerin, polyglycerin fatty acid ester, polyoxyethyleneglycerin isostearate, polyoxyethyleneglycerin monostearate, polyoxyethyleneglyceryl distearate, and polyoxyethyleneglyceryl tristearate.

For the water soluble ethylene type unsaturated monomer, joint use of a nonionic monomer and an ionic monomer (anionic monomer or cationic monomer) is preferable.

For the nonionic monomer, dialkylacrylamide is preferable.

For the ionic monomer, an anionic acrylamide derivative or a cationic acrylamide derivative is preferable.

Particularly preferable dialkylacrylamides are dimethylacrylamide and diethylacrylamide.

Particularly preferable ionic acrylamide derivatives are 2-acrylamido-2-methylpropanesulfonic acid and its salts.

A particularly preferable cationic acrylamide derivative is N,N-dimethylaminopropylacrylamidemethyl chloride.

The monomer composition ratio of the nonionic monomer and the ionic monomer in the polymerization system (feed ratio of the polymerization system) is selected based on the monomer composition ratio of the target microgel. The monomer composition ratio of the microgel and the feed ratio into the polymerization system are about the same. The feed ratio of the nonionic monomer and the ionic monomer in the polymerization system (molar ratio) for copolymerization is usually in the range of Nonionic monomer:Ionic monomer=0.5:9.5 to 9.5:0.5, preferably 1:9 to 9:1, more preferably 7:3 to 9:1. The optimum ratio is Nonionic monomer:Ionic monomer=8:2.

The aforementioned water soluble ethylene type unsaturated monomer is then chosen at will and the water-swelling polymer of the present invention is polymerized. A particularly preferable manufacturing method of the present invention polymerizes a water-swelling polymer consisting of a dipolymer microgel copolymerized from monomers of dimethylacrylamide and 2-acrylamido-2-methylpropanesulfonic acid, used as the water soluble ethylene type unsaturated monomer. The manufacturing method of the present invention does not require cross-linking monomers; a water-swelling polymer having a superior thickening effect is obtained by self cross-linking.

As described above, the manufacturing method of the present invention follows the following steps, for example, to manufacture the water-swelling polymer.

(1) The composition containing the water soluble ethylene type unsaturated monomer (dispersion phase) and the organic solvent or oil component (dispersion medium) is mixed with a surfactant and the temperature at which the electric conductivity becomes zero (phase transition temperature) is determined.

(2) The aforementioned surfactant (one type or a combination of two or more types) and its blend ratio are chosen in such a way that any temperature within 20° C. above this phase transition temperature (preferably a temperature higher than the phase transition temperature by 5-10° C.) is equal to the controllable desired arbitrary thermal radical polymerization temperature (preferably 30° C. or higher and 100° C. or lower).

(3) The thermal radical polymerization is carried out in the polymerization system composition chosen as described above while the temperature is maintained at the aforementioned controllable desired arbitrary thermal radical polymerization temperature. It is sufficient if the thermal radical polymerization temperature is maintained in the range no more than 20° C. above the aforementioned phase transition temperature; it is preferable to maintain the temperature 5-10° C. higher than the phase transition temperature.

(4) If the phase transition temperature of the polymerization system composition does not become equal to the controllable desired thermal radical polymerization temperature in the aforementioned method, the surfactant to be used in the polymerization system composition and its blend ratio are chosen by changing the dispersion medium organic solvent or oil component and/or adjusting the composition ratio of the water soluble ethylene type unsaturated monomer (water phase) and the organic solvent or oil component (oil phase).

The water-swelling polymer dispersed in water obtained by the polymerization method of the present invention has the rheological properties (1) and (2) below.

The apparent viscosity of the microgel aqueous dispersion having 0.5% (mass percentage) of the water-swelling polymer is 10,000 mPa·s or higher at a shear rate of $1.0\ s^{-1}$.

The dynamic elastic modulus of the water dispersion having 0.5% (mass percentage) of the water-swelling polymer satisfies the relationship G'>G" at a strain of 1% or less and a frequency range of 0.01-10 Hz.

The apparent viscosity of the microgel aqueous dispersion of the water-swelling polymer is the viscosity measured with a cone/plate rheometer (MCR-300 from Paar Physica) at 25° C. and a shear rate of $1.0\ s^{-1}$. The dynamic elastic modulus here means the stored elastic modulus (G') and the loss elastic modulus (G") measured at a strain of 1% or less and a frequency range of 0.01-10 Hz with the aforementioned measurement apparatus at a temperature of 25° C.

These physical properties can be measured not only with the aforementioned apparatus but also with a commercial rheometer.

EXAMPLES

The present invention is described in detail below by referring to Examples, but the present invention is not limited to these Examples. The blend ratios are in % (mass-percentage) units unless specified otherwise.

Invention of Claims 1-14

First, the synthesis examples of the microgel used in the present invention are described. The microgel obtained from a synthesis example is a thickener of the present invention. Polymer gels from comparative synthesis examples 1 and 2 prepared with a conventional homogeneous system polymerization method do not meet the requirements described in claims 1 and 2; they are not thickeners of the present invention.

Synthesis Example 1

40 g of dimethylacrylamide (from Kohjin) and 9 g of 2-acrylamido-2-methylpropanesulfonic acid (from Sigma) are dissolved in 250 g of ion-exchanged water and the pH is adjusted to 7.0 with sodium hydroxide. 250 g of n-hexane, 8.2 g of polyoxyethylene (3) oleyl ether (EMALEX 503 from Nihon Emulsion), and 16.4 g of polyoxyethylene (6) oleyl ether (EMALEX 506 from Nihon Emulsion) are put into a 1,000 ml three-neck flask equipped with a refluxing apparatus, mixed and dissolved, followed by $N_2$ substitution. The monomer aqueous solution is added to this three-neck flask, and the temperature is raised to 65° C.-70° C. using an oil bath as stirring is carried out in an $N_2$ atmosphere. When the system temperature reaches 65° C.-70° C., after confirming that the system has become a semitransparent microemulsion state, 2 g of ammonium persulfate is added to the polymerization system to start the polymerization. The temperature of the polymerization system is maintained at 65° C.-70° C. for three hours while stirring to obtain the microgel. After the completion of the polymerization, acetone is added to the microgel suspension to precipitate the microgel, followed by rinsing with acetone three times to remove the remaining monomers and the surfactant. The precipitate is filtered and then dried under a reduced pressure to obtain the dried microgel in a white powder form.

Synthesis Example 2

35 g of dimethylacrylamide (from Kohjin) and 17.5 g of 2-acrylamido-2-methylpropanesulfonic acid (from Sigma) are dissolved in 260 g of ion-exchanged water and the pH is adjusted to 7.0 with sodium hydroxide. 260 g of n-hexane, 8.7 g of polyoxyethylene (3) oleyl ether (EMALEX 503 from Nihon Emulsion), and 17.6 g of polyoxyethylene (6) oleyl ether (EMALEX 506 from Nihon Emulsion) are put into a 1,000 ml three-neck flask equipped with a refluxing apparatus, mixed and dissolved, followed by $N_2$ substitution. The monomer aqueous solution is added to this three-neck flask, and the temperature is raised to 65° C.-70° C. using an oil bath as stirring is carried out in an $N_2$ atmosphere. When the system temperature reaches 65° C.-70° C., after confirming that the system has become a semitransparent microemulsion state, 2 g of ammonium persulfate is added to the polymerization system to start the polymerization. The temperature of the polymerization system is maintained at 65° C.-70° C. for three hours while stirring to obtain the microgel. After the completion of the polymerization, acetone is added to the microgel suspension to precipitate the microgel, followed by rinsing with acetone three times to remove the remaining monomers and the surfactant. The precipitate is filtered and then dried under a reduced pressure to obtain the dried microgel in a white powder form.

Synthesis Example 3

30 g of dimethylacrylamide (from Kohjin) and 26.7 g of 2-acrylamido-2-methylpropanesulfonic acid (from Sigma) are dissolved in 280 g of ion-exchanged water and the pH is adjusted to 7.0 with sodium hydroxide. 280 g of n-hexane, 9.4 g of polyoxyethylene (3) oleyl ether (EMALEX 503 from Nihon Emulsion), and 19 g of polyoxyethylene (6) oleyl ether (EMALEX 506 from Nihon Emulsion) are put into a 1,000 ml three-neck flask equipped with a refluxing apparatus, mixed and dissolved, followed by $N_2$ substitution. The monomer aqueous solution is added to this three-neck flask, and the temperature is raised to 65° C.-70° C. using an oil bath as stirring is carried out in an $N_2$ atmosphere. When the system temperature reaches 65° C.-70° C., after confirming that the system has become a semitransparent microemulsion state, 2 g of ammonium persulfate is added to the polymerization system to start the polymerization. The temperature of the polymerization system is maintained at 65° C.-70° C. for three hours while stirring to obtain the microgel. After the completion of the polymerization, acetone is added to the microgel suspension to precipitate the microgel, followed by rinsing with acetone three times to remove the remaining monomers and the surfactant. The precipitate is filtered and then dried under a reduced pressure to obtain the dried microgel in a white powder form.

Synthesis Example 4

35 g of dimethylacrylamide (from Kohjin), 17.5 g of 2-acrylamido-2-methylpropanesulfonic acid (from Sigma), and 7 mg of methylenebisacrylamide are dissolved in 260 g of ion-exchanged water and the pH is adjusted to 7.0 with sodium hydroxide. 260 g of n-hexane, 8.7 g of polyoxyethylene (3) oleyl ether (EMALEX 503 from Nihon Emulsion), and 17.6 g of polyoxyethylene (6) oleyl ether (EMALEX 506 from Nihon Emulsion) are put into a 1,000 ml three-neck flask equipped with a refluxing apparatus, mixed and dissolved, followed by $N_2$ substitution. The monomer aqueous solution is added to this three-neck flask, and the temperature is raised to 65° C.-70° C. using an oil bath as stirring is carried out in an $N_2$ atmosphere. When the system temperature reaches 65° C.-70° C., after confirming that the system has become a semitransparent microemulsion state, 2 g of ammonium persulfate is added to the polymerization system to start the polymerization. The temperature of the polymerization system is maintained at 65° C.-70° C. for three hours while stirring to obtain the microgel. After the completion of the polymerization, acetone is added to the microgel suspension to precipitate the microgel, followed by rinsing with acetone three times to remove the remaining monomers and the surfactant. The precipitate is filtered and then dried under a reduced pressure to obtain the dried microgel in a white powder form.

Synthesis Example 5

35 g of dialkylacrylamide (from Kohjin), 17.5 g of 2-acrylamido-2-methylpropanesulfonic acid (from Sigma), and 70 mg of methylenebisacrylamide are dissolved in 260 g of ion-exchanged water and the pH is adjusted to 7.0 with sodium hydroxide. 260 g of n-hexane, 8.7 g of polyoxyethylene (3) oleyl ether (EMALEX 503 from Nihon Emulsion), and 17.6 g of polyoxyethylene (6) oleyl ether (EMALEX 506 from Nihon Emulsion) are put into a 1,000 ml three-neck flask equipped with a refluxing apparatus, mixed and dissolved, followed by $N_2$ substitution. The monomer aqueous solution is added to this three-neck flask, and the temperature is raised to 65° C.-70° C. using an oil bath as stirring is carried out in an $N_2$ atmosphere. When the system temperature reaches 65° C.-70° C., after confirming that the system has become a semitransparent microemulsion state, 2 g of ammonium persulfate is added to the polymerization system to start the polymerization. The temperature of the polymerization system is maintained at 65° C.-70° C. for three hours while stirring to obtain the microgel. After the completion of the polymerization, acetone is added to the microgel suspension to precipitate the microgel, followed by rinsing with acetone three times to remove the remaining monomers and the surfactant. The precipitate is filtered and then dried under a reduced pressure to obtain the dried microgel in a white powder form.

Synthesis Example 6

35 g of dialkylacrylamide (from Kohjin) and 17.5 g of N,N-dimethylaminopropylacrylamide methyl chloride (from Kohjin) are dissolved in 260 g of ion-exchanged water. 260 g of n-hexane, 8.7 g of polyoxyethylene (3) oleyl ether (EMALEX 503 from Nihon Emulsion), and 17.6 g of polyoxyethylene (6) oleyl ether (EMALEX 506 from Nihon Emulsion) are put into a 1,000 ml three-neck flask equipped with a refluxing apparatus, mixed and dissolved, followed by $N_2$ substitution. The monomer aqueous solution is added to this three-neck flask, and the temperature is raised to 65° C.-70° C. using an oil bath as stirring is carried out in an $N_2$ atmosphere. When the system temperature reaches 65° C.-70° C., after confirming that the system has become a semitransparent microemulsion state, 2 g of ammonium persulfate is added to the polymerization system to start the polymerization. The temperature of the polymerization system is maintained at 65° C.-70° C. for three hours while stirring to obtain the microgel. After the completion of the polymerization, acetone is added to the microgel suspension to precipitate the microgel, followed by rinsing with acetone three times to remove the remaining monomers and the surfactant. The precipitate is filtered and then dried under a reduced pressure to obtain the dried microgel in a white powder form.

Synthesis Example 7

35 g of dimethylacrylamide (from Kohjin), 17.5 g of N,N-dimethylaminopropylacrylamide methyl chloride (from Kohjin), and 7 mg of methylenebisacrylamide are dissolved in 260 g of ion-exchanged water. 260 g of n-hexane, 8.7 g of polyoxyethylene (3) oleyl ether (EMALEX 503 from Nihon Emulsion), and 17.6 g of polyoxyethylene (6) oleyl ether (EMALEX 506 from Nihon Emulsion) are put into a 1,000 ml three-neck flask equipped with a refluxing apparatus, mixed and dissolved, followed by $N_2$ substitution. The monomer aqueous solution is added to this three-neck flask, and the temperature is raised to 65° C.-70° C. using an oil bath as stirring is carried out in an $N_2$ atmosphere. When the system temperature reaches 65° C.-70° C., after confirming that the system has become a semitransparent microemulsion state, 2 g of ammonium persulfate is added to the polymerization system to start the polymerization. The temperature of the polymerization system is maintained at 65° C.-70° C. for three hours while stirring to obtain the microgel. After the completion of the polymerization, acetone is added to the microgel suspension to precipitate the microgel, followed by rinsing with acetone three times to remove the remaining monomers and the surfactant. The precipitate is filtered and then dried under a reduced pressure to obtain the dried microgel in a white powder form.

Comparative Synthesis Example 1

30 g of acrylamide (from Wako Pure Chemical Industries, ltd.) and 21.6 g of methacryloxyethylsulfonic acid (from Nippon Nyukazai) are dissolved in 260 g of ion-exchanged water. 260 g of n-hexane and 26 g of polyoxyethylene (3) oleyl ether (EMALEX 503 from Nihon Emulsion) are put into a 1,000 ml three-neck flask equipped with a refluxing apparatus, mixed and dissolved, followed by $N_2$ substitution. The monomer aqueous solution is added to this three-neck flask, and the temperature is raised to 65° C.-70° C. using an oil bath as stirring is carried out in an $N_2$ atmosphere; when the desired temperature is reached, 2 g of ammonium persulfate is added to the polymerization system to start the polymerization. The temperature of the polymerization system is maintained at 65° C.-70° C. for three hours while stirring to obtain the polymer. After the completion of the polymerization, acetone is added to the polymer suspension to precipitate the polymer, followed by rinsing with acetone three times to remove the remaining monomers and the surfactant. The precipitate is filtered and then dried under a reduced pressure to obtain the polymer in a lump form. This is then crushed by means of a bead mill to obtain a white powder.

Comparative Synthesis Example 2

30 g of acrylamide (from Wako Pure Chemical Industries, ltd.) and 21.6 g of methacryloxyethylsulfonic acid (from Nippon Nyukazai) are dissolved in 260 g of ion-exchanged water. 260 g of n-hexane and 26 g of polyoxyethylene (6) oleyl ether (EMALEX 506 from Nihon Emulsion) are put into a 1,000 ml three-neck flask equipped with a refluxing apparatus, mixed and dissolved, followed by $N_2$ substitution. The monomer aqueous solution is added to this three-neck flask, and the temperature is raised to 65° C.-70° C. using an oil bath as stirring is carried out in an $N_2$ atmosphere; when the desired temperature is reached, 2 g of ammonium persulfate is added to the polymerization system to start the polymerization. The temperature of the polymerization system is maintained at 65° C.-70° C. for three hours while stirring to obtain the aggregate (gel). After the completion of the polymerization, the aggregate (gel) is rinsed with acetone three times to remove the remaining monomers and the surfactant. The gel is filtered and then dried under a reduced pressure to obtain the dried gel in a lump form. This is then crushed by means of a bead mill to obtain a white powder.

"Effects as a Thickener"
(1) The Viscosity Behavior of the Microgel Dispersed in Water As an indicator of the thickening effect of the microgel obtained from Synthesis examples and Comparative synthesis examples, the viscosity behavior of the microgel dispersed in water was investigated. The microgels from Synthesis examples 1-7, Comparative synthesis examples 1-2, and a carboxyvinyl polymer (SYNTHALEN L from 3V SIGMA) were dispersed in ion-exchanged water to prepare 0.5 wt % water dispersions. A cone/plate rheometer (MCR-300 from Paar Physica) was used to measure the apparent viscosity of these microgel water dispersions at a shear rate of $1\ s^{-1}$. The measurement jig was a cone type having a diameter of 50 mm and an angle of 2 degrees; the measurement was carried out at a temperature of 25° C. The results are shown in Table 1.

and the water phase, in which the monomer is dissolved, becomes the continuous phase. When the polymerization proceeds under these conditions, a homogeneous gel will result. This gel is outside of the category of "microgel" used in the present invention and cannot be used as a thickener (Comparative example 2).

TABLE 1

|  | Example 1 | Example 2 | Example 6 | Example 4 | Example 5 | Example 6 | Example 7 | Comparative example 1 | Comparative example 2 | Comparative example 3 |
|---|---|---|---|---|---|---|---|---|---|---|
| Synthesis example 1 | 0.5 | | | | | | | | | |
| Synthesis example 2 | | 0.5 | | | | | | | | |
| Synthesis example 3 | | | 0.5 | | | | | | | |
| Synthesis example 4 | | | | 0.5 | | | | | | |
| Synthesis example 5 | | | | | 0.5 | | | | | |
| Synthesis example 6 | | | | | | 0.5 | | | | |
| Synthesis example 7 | | | | | | | 0.5 | | | |
| Comparative synthesis example 1 | | | | | | | | 0.5 | | |
| Comparative synthesis example 2 | | | | | | | | | 0.5 | |
| Carboxyvinyl polymer (from 3V SIGMA) | | | | | | | | | | 0.5 |
| Ion-exchanged water | to 100 | to 100 | to 100 | to 100 | to 100 | to 100 | to 100 | to 100 | to 100 | to 100 |
| Viscosity (mPa · s) | 28400 | 30700 | 31000 | 41300 | 29500 | 18700 | 20700 | 6800 | 1250 | 9800 |

All of the samples from Synthesis examples 1-7 exhibited a viscosity of 10,000 mPa·s or higher, indicating a satisfactory thickening effect. Surprisingly, a sufficient thickening effect is manifested even when a cross-linking monomer is not included in the copolymerization (Examples 1-3). Also, the thickening effect is shown to be 2-3 times more than that of a carboxyvinyl polymer (SYNTHALEN L: Comparative example 3) that is widely used today. A combination of 2-acrylamido-2-methylpropanesulfonic acid and a monomer other than dimethylacrylamide exhibits a low thickening effect unless a cross-linking monomer is used in the copolymerization.

In contrast, the results from Comparative examples 1 and 2, which contained the polymer powders from Comparative synthesis examples 1 and 2, clearly indicated the following:
a: When the HLB value of the surfactant is low, the clouding point of the polymerization system lowers and the particle size of the W/O emulsion at the time of the polymerization increases; a polymer polymerized in this condition is outside of the category of "microgel" as defined in the present invention and its thickening effect is low (Comparative example 1).
b: When the HLB value of the surfactant is high, the clouding point of the polymerization system rises and the system becomes an O/W emulsion at the time of the polymerization, This clearly indicates that the microgels of the synthesis examples used in the present invention exhibit a much higher thickening effect compared with conventional thickeners for cosmetics.

(2) The Viscosity Behavior of the Microgel Dispersed in Alcohol

The thickening effect in alcohol, which is one of the major characteristics of the microgel used in the present invention, was investigated. The test samples were dispersed in ethyl alcohol in such a way that the concentration was 0.5% (mass percentage) to prepare the alcohol dispersion of the microgel. A cone/plate rheometer (MCR-300 from Paar Physica) was used to measure the apparent viscosity of these microgel alcohol dispersions at a shear rate of $1\ s^{-1}$. The measurement jig was a cone type having a diameter of 50 mm and an angle of 2 degrees; the measurement was carried out at the temperature of 25° C. The results are shown in Table 2.

TABLE 2

|  | Example 8 | Example 9 | Example 10 | Comparative example 4 | Comparative example 5 | Comparative example 6 |
|---|---|---|---|---|---|---|
| Synthesis example 2 | 0.5 | | | | | |
| Synthesis example 4 | | 0.5 | | | | |
| Synthesis example 5 | | | 0.5 | | | |
| Comparative synthesis example 1 | | | | 0.5 | | |
| Comparative synthesis example 2 | | | | | 0.5 | |
| Carboxyvinyl polymer (from 3V SIGMA) | | | | | | 0.5 |
| Ethanol | to 100 | to 100 | to 100 | to 100 | to 100 | to 100 |
| Viscosity (mPa · s) | 7800 | 8100 | 6500 | Precipitation | Precipitation | 70 |

Carboxyvinyl polymer (SYNTHALEN L) can hardly thicken alcohol. Also, as shown in Comparative examples 4 and 5, the polymer powders of Comparative synthesis examples 1 and 2 precipitate completely in alcohol and cannot swell. On the contrary, the microgel used in the present invention was shown to be sufficiently capable of thickening alcohol or making alcohol into gel. It became clear that the thickening effect of the microgel in alcohol is manifested regardless of the presence or absence of a copolymerizing cross-linking monomer.

(3) The Dynamic Elastic Modulus of the Microgel Dispersion

One of the characteristics of a gel is that it behaves like a solid although it is mostly composed of liquid. Such a gel will retain its macroscopic mechanical properties even if it is finely crushed. For example, the inventors studied agar gel and compared the mechanical properties of bulk gel and gel obtained by crushing this bulk gel; and reported that qualitatively the crushed microgel shows the same properties as the bulk gel (Kaneda and Yanaki, Journal of the Society of Rheology, Japan vol. 30 No. 2, 89-94 2002).

Figure 3:
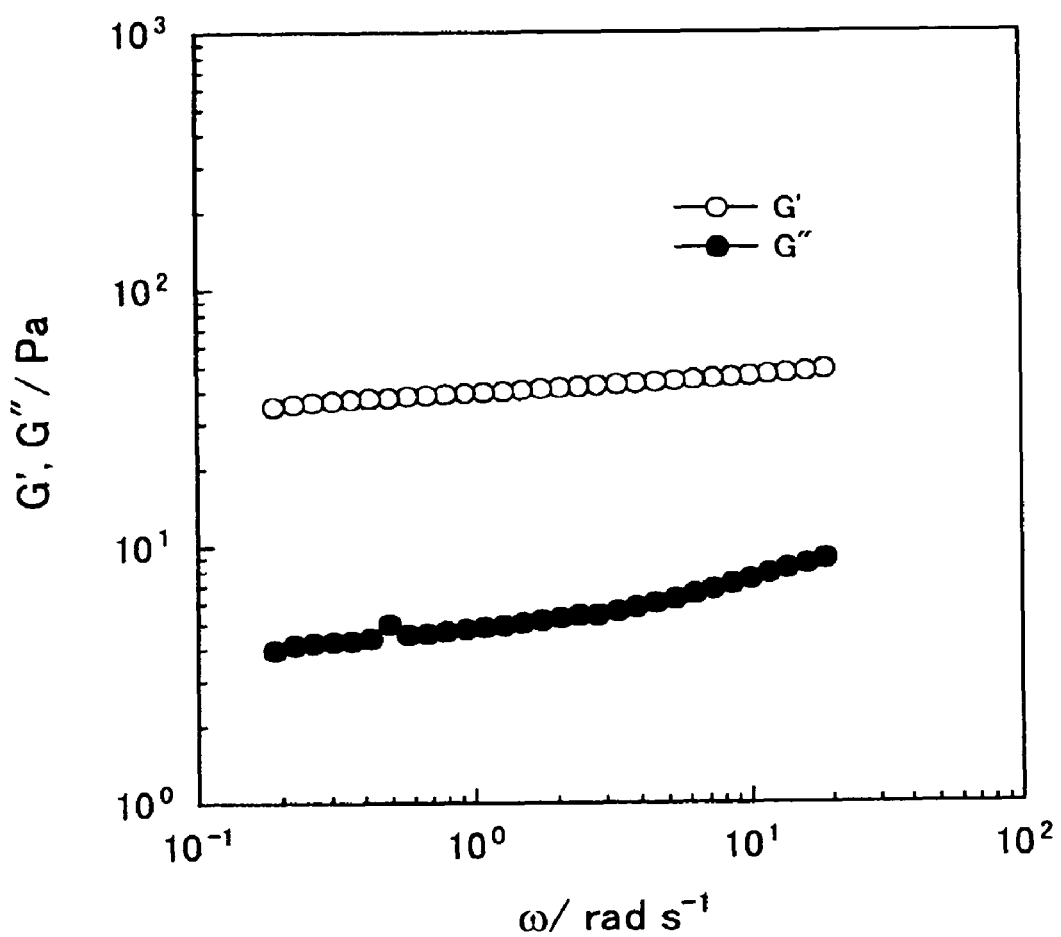
FIG. 3 is a graph showing the dynamic elastic modulus of ethanol.
Figure 4:
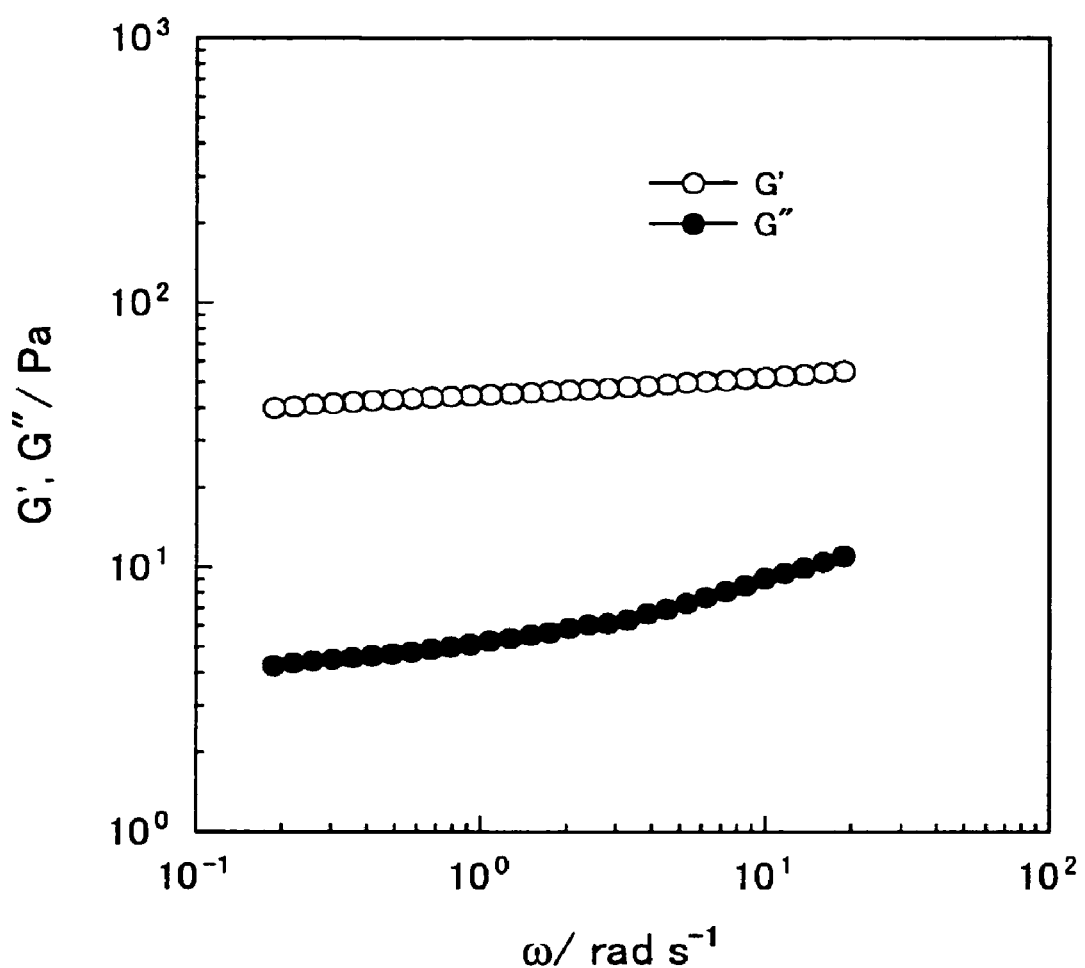
FIG. 4 is a graph showing the dynamic elastic modulus of a water/ethanol mixed solution.

That is, the dynamic elastic modulus measurement can verify that the fluid takes the form of a microgel. To clarify such physical properties of the present invention, the dynamic elastic modulus of the water dispersion and alcohol dispersion was measured. A cone/plate rheometer (MCR-300 from Paar Physica) was used to measure the dynamic elastic modulus at a shear rate of 1 $s^{-1}$, in a frequency range of 0.03-3 Hz and at 25° C. The microgel obtained from Synthesis example 2 was dispersed in water, ethanol, and a water/ethanol mixed solution (water:ethanol=20:80) to achieve a concentration of 0.5% (mass percentage), and the measured dynamic elastic modulus is shown in FIG. 3 (water), FIG. 4 (ethanol), and FIG. 5 (water/ethanol mixed solution).

The vertical axis of the graph indicates the stored elastic modulus G' (Pa) and the loss elastic modulus G" (Pa), and the horizontal axis indicates the angular frequency. The G' value indicates the solid-like properties of the test substance and the G" value indicates its liquid-like properties. That is, if G'>G" in this graph the substance can be semi-quantitatively determined to be solid-like (gel), and if G'<G" in this graph the substance can be semi-quantitatively determined to be liquid-like (sol).

All the results indicate typical gel-like properties, i.e. G' (stored elastic modulus)>G" (loss elastic modulus), within the measurement frequency range. This result shows that the high thickening effect indicated from the viscosity measurement results is due to the friction of fine microgel particles that exhibit the gel-like, i.e. solid-like, properties.

The samples in which the apparent viscosity at 1 $s^{-1}$ was low did not exhibit such gel-like behavior in terms of the dynamic elastic modulus.

(4) Functions as an Acid Resistant Thickener

Figure 5:
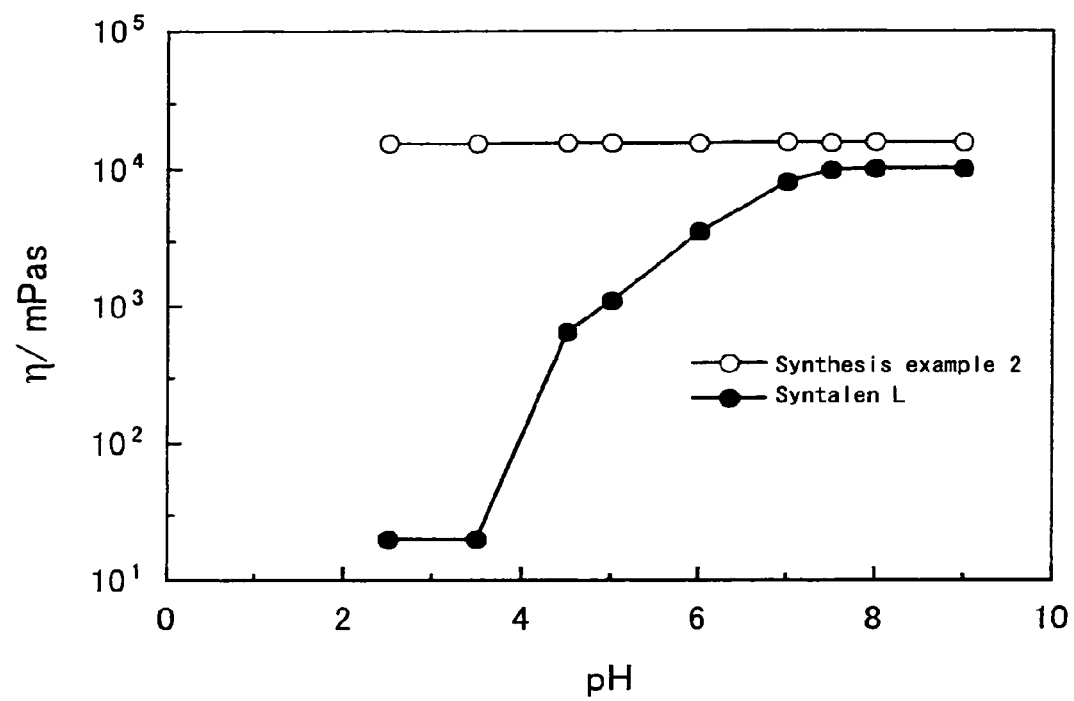
FIG. 5 is a graph showing the relationship between the viscosity and pH.

A microgel that contains sulfonic acid as a copolymerized monomer is expected to exhibit a stable thickening effect over a wide pH range. Synthesis example 2 and a 0.5% (mass percentage) SYNTHALEN L water dispersion were tested for their viscosity behavior at various pHs. The measurement was carried out in the same manner as in the aforementioned (1) and the viscosity at a shear rate of 1 $s^{-1}$ and at a temperature of 25° C. was measured. The result is shown in FIG. 5. The microgel of Synthesis example 2 showed a stable thickening effect in the range of pH=2-11.

(5) Sensation During Use when Blended in a Cosmetic

The sensation during use was investigated for cosmetics containing the microgel which is a thickener of the present invention. The test sample was blended in a typical cream recipe and three specialized panelists conducted the sensory evaluation of the tactile sensation during use. The evaluation was carried out for three criteria, i.e. "tactile sensation at the time of applications, &non-stickiness when almost dry", and "comprehensive evaluation", by using the following criteria.

4 points: Exceptionally superior
3 points: Superior
2 points: Hard to say whether superior or inferior
1 point: Inferior
◎: The average score is 3.5 points or more and 4 points or less.
○: The average score is 3 points or more and less than 3.5 points.
Δ: 2 points or more and less than 3
X: Less than 2 points The recipes shown in Table 3 were used in a conventional method to prepare W/O emulsified creams.

The results are shown in Table 3. Cosmetics containing the microgel of the present invention as a thickener received much higher ratings in terms of the sensation during use compared with cosmetics containing conventional thickeners.

TABLE 3

|  | Example 11 | Example 12 | Example 13 | Example 14 | Comparative example 9 | Comparative example 10 |
|---|---|---|---|---|---|---|
| Ion-exchanged water | to 100 | to 100 | to 100 | to 100 | to 100 | to 100 |
| Synthesis example 2 | 0.5 | | | | | |
| Synthesis example 4 | | 0.5 | | | | |
| Synthesis example 6 | | | 0.5 | | | |
| Synthesis example 7 | | | | 0.5 | | |
| Carboxyvinyl polymer*[1] | | | | | 0.5 | |
| Xanthan gum*[2] | | | | | | 0.5 |
| 10% KOH | | | | | 1.88 | |
| 1,3-BG | 5.00 | 5.00 | 5.00 | 5.00 | 5.00 | 5.00 |
| Stearic acid | 0.3 | 0.3 | 0.3 | 0.3 | 0.3 | 0.3 |
| Behenic acid | 0.45 | 0.45 | 0.45 | 0.45 | 0.45 | 0.45 |
| Behenyl alcohol | 1.5 | 1.5 | 1.5 | 1.5 | 1.5 | 1.5 |
| Ethylparaben | 0.18 | 0.18 | 0.18 | 0.18 | 0.18 | 0.18 |
| Butylparaben | 0.1 | 0.1 | 0.1 | 0.1 | 0.1 | 0.1 |
| Glyceryl stearate | 1.65 | 1.65 | 1.65 | 1.65 | 1.65 | 1.65 |
| Squalane | 10 | 10 | 10 | 10 | 10 | 10 |
| Isostearic acid | 0.45 | 0.45 | 0.45 | 0.45 | 0.45 | 0.45 |
| Liquid petrolatum | 6 | 6 | 6 | 6 | 6 | 6 |
| Polyoxyethylene (5) glyceryl monostearate*[3] | 1.14 | 1.14 | 1.14 | 1.14 | 1.14 | 1.14 |
| Dimethyl polysiloxane*[4] | 6 | 6 | 6 | 6 | 6 | 6 |
| Sensation at the time of application | ◎ | ◎ | ◎ | ◎ | ◎ | ○ |

TABLE 3-continued

|  | Example 11 | Example 12 | Example 13 | Example 14 | Comparative example 9 | Comparative example 10 |
|---|---|---|---|---|---|---|
| Stickiness when it is almost dry | ◎ | ◎ | ◎ | ◎ | X | X |
| Comprehensive rating | ◎ | ◎ | ◎ | ◎ | ○ | Δ |

*[1]Carboxyvinyl polymer (from 3V SIGMA)
*[2]KELTOROL (from Kelco)
*[3]EMALEX GM-5 (from Nihon Emulsion)
*[4]Silicone KF-96-AT (from Shin-Etsu Chemical Co., Ltd.)

Examples of the cosmetic containing the thickener of the present invention are shown below. Prepared with a conventional method, these cosmetics all exhibit a superior thickening effect and give a superior sensation during use; also, they have no problems in terms of external appearance.

Table 4 shows Examples of whitening emulsions containing the thickeners prepared in Synthesis examples 1-7. Stable thickening can be achieved with O/W emulsified compositions as well. There is no problem in terms of the sensation during use and external appearance.

TABLE 4

|  | Example 15 | Example 16 | Example 17 | Example 18 | Example 19 | Example 20 | Example 21 |
|---|---|---|---|---|---|---|---|
| Liquid petrolatum | 5 | 5 | 5 | 5 | 5 | 5 | 5 |
| Dimethylpolysiloxane | 3 | 3 | 3 | 3 | 3 | 3 | 3 |
| Squalane | 2 | 2 | 2 | 2 | 2 | 2 | 2 |
| Glycerin | 8 | 8 | 8 | 8 | 8 | 8 | 8 |
| Hydrogenated castor oil | 2 | 2 | 2 | 2 | 2 | 2 | 2 |
| Citric acid | 0.01 | 0.01 | 0.01 | 0.01 | 0.01 | 0.01 | 0.01 |
| Sodium citrate | 0.09 | 0.09 | 0.09 | 0.09 | 0.09 | 0.09 | 0.09 |
| Diglycoside ascorbate | 2 | 2 | 2 | 2 | 2 | 2 | 2 |
| Methylparaben | 0.3 | 0.3 | 0.3 | 0.3 | 0.3 | 0.3 | 0.3 |
| Synthesis example 1 | 0.1 |  |  |  |  |  |  |
| Synthesis example 2 |  | 0.1 |  |  |  |  |  |
| Synthesis example 3 |  |  | 0.1 |  |  |  |  |
| Synthesis example 4 |  |  |  | 0.1 |  |  |  |
| Synthesis example 5 |  |  |  |  | 0.1 |  |  |
| Synthesis example 6 |  |  |  |  |  | 0.1 |  |
| Synthesis example 7 |  |  |  |  |  |  | 0.1 |
| Ion-exchanged water | to 100 | to 100 | to 100 | to 100 | to 100 | to 100 | to 100 |

Table 5 shows Examples of clear water type body gels containing dipropylene glycol (DPG) and/or polyethylene glycol (PEG1500) as a humectant and also a high concentration of alcohol (ethanol). Stable thickening is achieved by blending in the thickeners of Synthesis examples 1-7. Also, a beautiful body gel with a homogeneous and clear appearance can be obtained. However, if the thickeners of Comparative synthesis examples are used, then thickening is not possible due to a high concentration of alcohol. Also, in terms of external appearance, the thickener particles are visible.

TABLE 5

|  | Example 22 | Example 23 | Example 24 | Example 25 | Example 26 | Example 27 | Example 28 | Comparative example 11 | Comparative example 12 |
|---|---|---|---|---|---|---|---|---|---|
| DPG | 5 | 5 | 5 | 5 | 5 | 5 | 5 | 5 | 5 |
| PEG 1500 | 6 | 6 | 6 | 6 | 6 | 6 | 6 | 6 | 6 |
| Alcohol | 50 | 50 | 50 | 50 | 50 | 50 | 50 | 50 | 50 |
| Synthesis example 1 | 0.5 |  |  |  |  |  |  |  |  |
| Synthesis example 2 |  | 0.5 |  |  |  |  |  |  |  |
| Synthesis example 3 |  |  | 0.5 |  |  |  |  |  |  |
| Synthesis example 4 |  |  |  | 0.5 |  |  |  |  |  |
| Synthesis example 5 |  |  |  |  | 0.5 |  |  |  |  |
| Synthesis example 6 |  |  |  |  |  | 0.5 |  |  |  |
| Synthesis example 7 |  |  |  |  |  |  | 0.5 |  |  |

TABLE 5-continued

| | Example 22 | Example 23 | Example 24 | Example 25 | Example 26 | Example 27 | Example 28 | Comparative example 11 | Comparative example 12 |
|---|---|---|---|---|---|---|---|---|---|
| Comparative synthesis example 1 | | | | | | | | 0.5 | |
| Comparative synthesis example 1 | | | | | | | | | 0.5 |
| Ion-exchanged water | to 100 | to 100 | to 100 | to 100 | to 100 | to 100 | to 100 | to 100 | to 100 |
| Viscosity | 18600 | 19000 | 19200 | 20000 | 18900 | 23000 | 20000 | 650 | 340 |
| External appearance | Homogeneous and clear | Homogeneous and clear | Homogeneous and clear | Homogeneous and clear | Homogeneous and clear | Homogeneous and clear | Homogeneous and clear | Grainy | Grainy |

Table 6 shows Examples of acidic hair dyes. The thickeners obtained in Synthesis examples 1-5 are blended in these Examples since cationic polymers cannot be blended in. The thickener of the present invention exhibits a superior thickening effect even in acidic compositions such as acidic hair dyes, providing a hair dye with a required thickening effect, as well as superior sensation during use and external appearance. Carboxyvinyl polymer, which is a conventional thickener, cannot exhibit a stable thickening effect in acidic compositions.

TABLE 6

| | Example 29 | Example 30 | Example 31 | Example 32 | Example 33 |
|---|---|---|---|---|---|
| Acidic dye | 1 | 1 | 1 | 1 | 1 |
| Benzyl alcohol | 6 | 6 | 6 | 6 | 6 |
| Isopropyl alcohol | 20 | 20 | 20 | 20 | 20 |
| Citric acid | 0.5 | 0.5 | 0.5 | 0.5 | 0.5 |

TABLE 6-continued

| | Example 29 | Example 30 | Example 31 | Example 32 | Example 33 |
|---|---|---|---|---|---|
| Synthesis example 1 | 0.6 | | | | |
| Synthesis example 2 | | 0.6 | | | |
| Synthesis example 3 | | | 0.6 | | |
| Synthesis example 4 | | | | 0.6 | |
| Synthesis example 5 | | | | | 0.6 |
| Ion-exchanged water | to 100 | to 100 | to 100 | to 100 | to 100 |

Table 7 shows Examples of two-component acidic hair dyes. The thickeners obtained in Synthesis examples 1-5 are blended in these Examples since cationic polymers cannot be blended in. These hair dyes give the thickening effect required for hair dyes as well as a superior sensation during use and superior external appearance.

TABLE 7

| | | | | | |
|---|---|---|---|---|---|
| Paraphenylenediamine | | | 3 | | |
| Resorcin | | | 0.5 | | |
| Oleic acid | | | 20 | | |
| POE (10) oleyl ether | | | 15 | | |
| Isopropyl alcohol | | | 10 | | |
| Aqueous ammonia (28%) | | | 10 | | |
| Chelating agnet | | | Appropriate amount | | |
| Ion-exchanged water | | | to 100 | | |

| | Example 34 | Example 35 | Example 36 | Example 37 | Example 38 |
|---|---|---|---|---|---|
| Hydrogen peroxide solution (30%) | 20 | 20 | 20 | 20 | 20 |
| Stabilizer | Appropriate amount | Appropriate amount | Appropriate amount | Appropriate amount | Appropriate amount |
| Synthesis example 1 | 1 | | | | |
| Synthesis example 2 | | 1 | | | |
| Synthesis example 3 | | | 1 | | |
| Synthesis example 4 | | | | 1 | |
| Synthesis example 5 | | | | | 1 |
| Ion-exchanged water | to 100 | to 100 | to 100 | to 100 | to 100 |

Table 8 shows Examples of hair gels containing the thickeners prepared in Synthesis examples 1-7. In all of these Examples, a stable thickening effect and superior sensation during use and external appearance are achieved.

TABLE 8

|  | Example 39 | Example 40 | Example 41 | Example 42 | Example 43 | Example 44 | Example 45 |
|---|---|---|---|---|---|---|---|
| Polyvinylpyrrolidone | 2 | 2 | 2 | 2 | 2 | 2 | 2 |
| Glycerin | 2 | 2 | 2 | 2 | 2 | 2 | 2 |
| Alcohol | 30 | 30 | 30 | 30 | 30 | 30 | 30 |
| Hydrogenated castor oil | 0.5 | 0.5 | 0.5 | 0.5 | 0.5 | 0.5 | 0.5 |
| Synthesis example 1 | 0.6 | | | | | | |
| Synthesis example 2 | | 0.6 | | | | | |
| Synthesis example 3 | | | 0.6 | | | | |
| Synthesis example 4 | | | | 0.6 | | | |
| Synthesis example 5 | | | | | 0.6 | | |
| Synthesis example 6 | | | | | | 0.6 | |
| Synthesis example 7 | | | | | | | 0.6 |
| Ion-exchanged water | to 100 | to 100 | to 100 | to 100 | to 100 | to 100 | to 100 |

Examples of aftershave lotions containing a high concentration of alcohol (ethanol) are shown in Table 9. The thickener of the present invention exhibits an exceptionally superior thickening effect for thickening cosmetics requiring a high concentration of alcohol such as aftershave lotions. The thickeners obtained from Comparative synthesis examples 1 and 2 cannot thicken cosmetics with a high concentration of alcohol.

TABLE 9

|  | Example 46 | Example 47 | Example 48 | Example 49 | Example 50 | Example 51 | Example 52 |
|---|---|---|---|---|---|---|---|
| Alcohol | 60 | 60 | 60 | 60 | 60 | 60 | 60 |
| Dipropylene glycol | 2 | 2 | 2 | 2 | 2 | 2 | 2 |
| Hydrogenated castor oil | 1 | 1 | 1 | 1 | 1 | 1 | 1 |
| Allantoin | 0.1 | 0.1 | 0.1 | 0.1 | 0.1 | 0.1 | 0.1 |
| *Aloe* extract | Appropriate amount | Appropriate amount | Appropriate amount | Appropriate amount | Appropriate amount | Appropriate amount | Appropriate amount |
| Synthesis example 1 | 0.6 | | | | | | |
| Synthesis example 2 | | 0.6 | | | | | |
| Synthesis example 3 | | | 0.6 | | | | |
| Synthesis example 4 | | | | 0.6 | | | |
| Synthesis example 5 | | | | | 0.6 | | |
| Synthesis example 6 | | | | | | 0.6 | |
| Synthesis example 7 | | | | | | | 0.6 |
| Ion-exchanged water | to 100 | to 100 | to 100 | to 100 | to 100 | to 100 | to 100 |

Examples of hair tonics containing a high concentration of alcohol (ethanol) are shown in Table 10. The thickener of the present invention exhibits an exceptionally superior thickening effect for thickening cosmetics requiring a high concentration of alcohol such as hair tonics. The thickeners obtained from Comparative synthesis examples 1 and 2 cannot thicken cosmetics with a high concentration of alcohol.

TABLE 10

|  | Example 53 | Example 54 | Example 55 | Example 56 | Example 57 | Example 58 | Example 59 |
|---|---|---|---|---|---|---|---|
| Alcohol | 60 | 60 | 60 | 60 | 60 | 60 | 60 |
| Hinokitiol | Appropriate amount | Appropriate amount | Appropriate amount | Appropriate amount | Appropriate amount | Appropriate amount | Appropriate amount |
| *Swertia japonica* extract | Appropriate amount | Appropriate amount | Appropriate amount | Appropriate amount | Appropriate amount | Appropriate amount | Appropriate amount |
| Vitamin E | Appropriate amount | Appropriate amount | Appropriate amount | Appropriate amount | Appropriate amount | Appropriate amount | Appropriate amount |
| Propylene glycol | 2 | 2 | 2 | 2 | 2 | 2 | 2 |
| Synthesis example 1 | 0.4 | | | | | | |
| Synthesis example 2 | | 0.4 | | | | | |
| Synthesis example 3 | | | 0.4 | | | | |
| Synthesis example 4 | | | | 0.4 | | | |
| Synthesis example 5 | | | | | 0.4 | | |
| Synthesis example 6 | | | | | | 0.4 | |
| Synthesis example 7 | | | | | | | 0.4 |
| Ion-exchanged water | to 100 | to 100 | to 100 | to 100 | to 100 | to 100 | to 100 |

Table 11 shows Examples of clear gel self tanning cosmetics containing the thickeners prepared in Synthesis examples 1-7. The self tanning base agents containing the thickeners of Synthesis examples 1-7 can provide a beautiful gel with a clear and homogeneous external appearance.

Regarding the sensation during use, the sensory evaluation of the tactile sensation during use was performed by three specialized panelists. The evaluation rating was determined based on the following criteria.

4 points: Exceptionally superior, 3 points: Superior, 2 points: Hard to say whether superior or inferior, and 1 point: Inferior.

◉: The average rating is 3.5 or more and 4 or less; ○: The average rating is 3 or more and less than 3.5; Δ: 2 or more and less than 3; X: Less than 2.

They give a superior sensation at the time of application, exhibit stable viscosity and a superior degree of dyeing, resulting in a superior comprehensive rating.

TABLE 11

| | Example 60 | Example 61 | Example 62 | Example 63 | Example 64 | Example 65 | Example 66 | Comparative example 13 | Comparative example 14 |
|---|---|---|---|---|---|---|---|---|---|
| Ion-exchanged water | Balance | Balance | Balance | Balance | Balance | Balance | Balance | Balance | Balance |
| Sodium pyrosulfite | 0.02 | 0.02 | 0.02 | 0.02 | 0.02 | 0.02 | 0.02 | 0.02 | 0.02 |
| EDTA2Na•2H$_2$O | 0.03 | 0.03 | 0.03 | 0.03 | 0.03 | 0.03 | 0.03 | 0.03 | 0.03 |
| Dihydroxyacetone | 3 | 3 | 3 | 3 | 3 | 3 | 3 | 3 | 3 |
| 1,3-BG | 5 | 5 | 5 | 5 | 5 | 5 | 5 | 5 | 5 |
| Dynamite glycerin | 2 | 2 | 2 | 2 | 2 | 2 | 2 | 2 | 2 |
| Methylparaben | 0.17 | 0.17 | 0.17 | 0.17 | 0.17 | 0.17 | 0.17 | 0.17 | 0.17 |
| Phenoxyethanol | 0.3 | 0.3 | 0.3 | 0.3 | 0.3 | 0.3 | 0.3 | 0.3 | 0.3 |
| L-menthol | 0.005 | 0.02 | 0.02 | 0.02 | 0.02 | 0.02 | 0.02 | 0.02 | 0.02 |
| Ethanol | 5 | 5 | 5 | 5 | 5 | 5 | 5 | 5 | 5 |
| Caramel | 0.2 | 0.2 | 0.2 | 0.2 | 0.2 | 0.2 | 0.2 | 0.2 | 0.2 |
| Caffeine | 0.01 | 0.01 | 0.01 | 0.01 | 0.01 | 0.01 | 0.01 | 0.01 | 0.01 |
| Synthesis example 1 | 0.8 | | | | | | | | |
| Synthesis example 2 | | 0.8 | | | | | | | |
| Synthesis example 3 | | | 0.8 | | | | | | |
| Synthesis example 4 | | | | 0.8 | | | | | |
| Synthesis example 5 | | | | | 0.8 | | | | |
| Synthesis example 6 | | | | | | 0.8 | | | |
| Synthesis example 7 | | | | | | | 0.8 | | |
| Carboxyvinyl polymer | | | | | | | | 0.8 | |
| Xanthan gum | | | | | | | | | 0.8 |
| Sensation at the time of application | ◉ | ◉ | ◉ | ◉ | ◉ | ◉ | ◉ | ○ | Δ |
| Stability of viscosity | ◉ | ◉ | ◉ | ◉ | ◉ | ◉ | ◉ | X | ○ |
| Degree of dyeing | ◉ | ◉ | ◉ | ◉ | ◉ | ◉ | ◉ | Δ | X |
| Comprehensive rating | ◉ | ◉ | ◉ | ◉ | ◉ | ◉ | ◉ | Δ | X |

Table 12 shows Examples of clear gel self tanning cosmetics containing the thickeners prepared in Synthesis examples 1-7. The self tanning base agents containing the thickeners of Synthesis examples 1-7 can provide an emulsified composition with a beautiful external appearance.

Regarding the sensation during use, the sensory evaluation of the tactile sensation during use was performed by three specialized panelists. The evaluation rating was determined based on the following criteria.

4 points: Exceptionally superior, 3 points: Superior, 2 points: Hard to say whether superior or inferior, and 1 point: Inferior.

◉: The average rating is 3.5 or more and 4 or less; ○: The average rating is 3 or more and less than 3.5; Δ: 2 or more and less than 3; X: Less than 2.

They give a superior sensation at the time of application, exhibit stable viscosity and a superior degree of dyeing, resulting in a superior comprehensive rating.

TABLE 12

| | Example 67 | Example 68 | Example 69 | Example 70 | Example 71 | Example 72 | Example 73 | Comparative example 15 | Comparative example 16 |
|---|---|---|---|---|---|---|---|---|---|
| Ion-exchanged water | Balance | Balance | Balance | Balance | Balance | Balance | Balance | Balance | Balance |
| Sodium pyrosulfite | 0.02 | 0.02 | 0.02 | 0.02 | 0.02 | 0.02 | 0.02 | 0.02 | 0.02 |
| EDTA2Na•2H$_2$O | 0.03 | 0.04 | 0.04 | 0.04 | 0.04 | 0.04 | 0.04 | 0.04 | 0.04 |
| Dihydroxyacetone | 5 | 5 | 5 | 5 | 5 | 5 | 5 | 5 | 5 |
| 1,3-BG | 5 | 7.2 | 7.2 | 7.2 | 7.2 | 7.2 | 7.2 | 7.2 | 7.2 |
| Dynamite glycerin | 2 | 3 | 3 | 3 | 3 | 3 | 3 | 3 | 3 |

TABLE 12-continued

| | Example 67 | Example 68 | Example 69 | Example 70 | Example 71 | Example 72 | Example 73 | Comparative example 15 | Comparative example 16 |
|---|---|---|---|---|---|---|---|---|---|
| Methylparaben | 0.17 | 0.24 | 0.24 | 0.24 | 0.24 | 0.24 | 0.24 | 0.24 | 0.24 |
| Phenoxyethanol | 0.3 | 0.3 | 0.3 | 0.3 | 0.3 | 0.3 | 0.3 | 0.3 | 0.3 |
| Synthesis example 1 | 0.8 | | | | | | | | |
| Synthesis example 2 | | 0.8 | | | | | | | |
| Synthesis example 3 | | | 0.8 | | | | | | |
| Synthesis example 4 | | | | 0.8 | | | | | |
| Synthesis example 5 | | | | | 0.8 | | | | |
| Synthesis example 6 | | | | | | 0.8 | | | |
| Synthesis example 7 | | | | | | | 0.8 | | |
| Carboxyvinyl polymer | | | | | | | | 0.8 | |
| Xanthan gum | | | | | | | | | 0.8 |
| Polyoxyethylene polyoxypropylene cetyl ether | 0.5 | 0.5 | 0.5 | 0.5 | 0.5 | 0.5 | 0.5 | 0.5 | 0.5 |
| Decamethylcyclopentasiloxane | 5 | 5 | 5 | 5 | 5 | 5 | 5 | 5 | 5 |
| Sensation at the time of application | ◎ | ◎ | ◎ | ◎ | ◎ | ◎ | ◎ | ○ | X |
| Stability of viscosity | ◎ | ◎ | ◎ | ◎ | ◎ | ◎ | ◎ | X | ○ |
| Degree of dyeing | ◎ | ◎ | ◎ | ◎ | ◎ | ◎ | ◎ | Δ | X |
| Comprehensive rating | ◎ | ◎ | ◎ | ◎ | ◎ | ◎ | ◎ | Δ | X |

Table 13 shows Examples of O/W type self tanning cosmetics containing the thickeners prepared in Synthesis examples 1-7. The self tanning base agents containing the thickeners of Synthesis examples 1-7 can provide a stable emulsified composition containing powder.

Regarding the sensation during use, the sensory evaluation of the tactile sensation during use was performed by three specialized panelists. The evaluation rating was determined based on the following criteria.

4 points: Exceptionally superior, 3 points: Superior, 2 points: Hard to say whether superior or inferior, and 1 point: Inferior.

◎: The average rating is 3.5 or more and 4 or less; ○: The average rating is 3 or more and less than 3.5; Δ: 2 or more and less than 3; X: Less than 2.

They give a superior sensation at the time of application, exhibit stable viscosity and a superior degree of dyeing, thus resulting in a superior comprehensive rating.

TABLE 13

| | Example 74 | Example 75 | Example 76 | Example 77 | Example 78 | Comparative example 17 | Comparative example 18 |
|---|---|---|---|---|---|---|---|
| Ion-exchanged water | Balance | Balance | Balance | Balance | Balance | Balance | Balance |
| Sodium pyrosulfite | 0.02 | 0.02 | 0.02 | 0.02 | 0.02 | 0.02 | 0.02 |
| EDTA2Na•2H$_2$O | 0.03 | 0.03 | 0.03 | 0.03 | 0.03 | 0.03 | 0.03 |
| Dihydroxyacetone | 5 | 5 | 5 | 5 | 5 | 5 | 5 |
| Dynamite glycerin | 2 | 2 | 2 | 2 | 2 | 2 | 2 |
| 1,3-BG | 4 | 4 | 4 | 4 | 4 | 4 | 4 |
| Methylparaben | 0.15 | 0.15 | 0.15 | 0.15 | 0.15 | 0.15 | 0.15 |
| Phenoxyethanol | 0.3 | 0.3 | 0.3 | 0.3 | 0.3 | 0.3 | 0.3 |
| Hydrogenated castor oil | 2 | 2 | 2 | 2 | 2 | 2 | 2 |
| Synthesis example 1 | 0.7 | | | | | | |
| Synthesis example 2 | | 0.7 | | | | | |
| Synthesis example 3 | | | 0.7 | | | | |
| Synthesis example 4 | | | | 0.7 | | | |
| Synthesis example 5 | | | | | 0.7 | | |
| Carboxyvinyl polymer | | | | | | 0.7 | |
| Xanthan gum | | | | | | | 0.7 |
| Decamethylcyclopentasiloxane | 5 | 5 | 5 | 5 | 5 | 5 | 5 |
| Methylphenylpolysiloxane | 1 | 1 | 1 | 1 | 1 | 1 | 1 |
| Cetyl 2-ethylhexanoate | 4 | 4 | 4 | 4 | 4 | 4 | 4 |
| Polyoxyethylene/methylpolysiloxane copolymer | 6.6 | 6.6 | 6.6 | 6.6 | 6.6 | 6.6 | 6.6 |
| Dimethylsiloxane/polyalkylene glycol copolymer | 0.2 | 0.2 | 0.2 | 0.2 | 0.2 | 0.2 | 0.2 |
| Isostearic acid | 0.5 | 0.5 | 0.5 | 0.5 | 0.5 | 0.5 | 0.5 |
| Octyl paramethoxycinnamate | 7.5 | 7.5 | 7.5 | 7.5 | 7.5 | 7.5 | 7.5 |
| Titanium oxide | 15 | 15 | 15 | 15 | 15 | 15 | 15 |
| Sensation at the time of application | ◎ | ◎ | ◎ | ◎ | ◎ | ○ | Δ |
| Stability of viscosity | ◎ | ◎ | ◎ | ◎ | ◎ | X | ○ |
| Degree of dyeing | ◎ | ◎ | ◎ | ◎ | ◎ | X | X |
| Comprehensive rating | ◎ | ◎ | ◎ | ◎ | ◎ | Δ | X |

Table 14 shows Examples of an O/W type liquid foundation containing the thickeners prepared in Synthesis examples 1-7. The O/W type liquid foundations containing the thickeners of Synthesis examples 1-7 provided stable emulsified compositions.

Regarding the sensation during use, the sensory evaluation of the tactile sensation during use was performed by three specialized panelists. The evaluation rating was determined based on the following criteria.

4 points: Exceptionally superior, 3 points: Superior, 2 points: Hard to say whether superior or inferior, and 1 point: Inferior.

◎: The average rating is 3.5 or more and 4 or less; ○: The average rating is 3 or more and less than 3.5; Δ: 2 or more and less than 3; X: Less than 2.

These foundations give a superior sensation at the time of application and exhibit stable viscosity over time, resulting in a superior comprehensive rating.

TABLE 14

| | Example 79 | Example 80 | Example 81 | Example 82 | Example 83 | Example 84 | Example 85 | Comparative example 19 | Comparative example 20 |
|---|---|---|---|---|---|---|---|---|---|
| Purified water | Balance | Balance | Balance | Balance | Balance | Balance | Balance | Balance | Balance |
| Synthesis example 1 | 2 | | | | | | | | |
| Synthesis example 2 | | 2 | | | | | | | |
| Synthesis example 3 | | | 2 | | | | | | |
| Synthesis example 4 | | | | 2 | | | | | |
| Synthesis example 5 | | | | | 2 | | | | |
| Synthesis example 6 | | | | | | 2 | | | |
| Synthesis example 7 | | | | | | | 2 | | |
| Carboxyvinyl polymer | | | | | | | | 2 | |
| Xanthan gum | | | | | | | | | 2 |
| Glycerin | 10 | 10 | 10 | 10 | 10 | 10 | 10 | 10 | 10 |
| Polyoxyethylene (20) sorbitan monostearate | 2 | 2 | 2 | 2 | 2 | 2 | 2 | 2 | 2 |
| Sodium hexamethaphosphate | 1 | 1 | 1 | 1 | 1 | 1 | 1 | 1 | 1 |
| EDTA | 0.5 | 0.5 | 0.5 | 0.5 | 0.5 | 0.5 | 0.5 | 0.5 | 0.5 |
| Preservative | 0.5 | 0.5 | 0.5 | 0.5 | 0.5 | 0.5 | 0.5 | 0.5 | 0.5 |
| Decamethyl-cyclopentasiloxane | 3 | 3 | 3 | 3 | 3 | 3 | 3 | 3 | 3 |
| Dodecamethyl-cyclohexasiloxane | 2.5 | 2.5 | 2.5 | 2.5 | 2.5 | 2.5 | 2.5 | 2.5 | 2.5 |
| Trioctanoin | 2 | 2 | 2 | 2 | 2 | 2 | 2 | 2 | 2 |
| Poly-dimethylsiloxane | 2 | 2 | 2 | 2 | 2 | 2 | 2 | 2 | 2 |
| Polymethyl-phenylsiloxane | 1 | 1 | 1 | 1 | 1 | 1 | 1 | 1 | 1 |
| Squalane | 1 | 1 | 1 | 1 | 1 | 1 | 1 | 1 | 1 |
| Iron oxide | 2.2 | 2.2 | 2.2 | 2.2 | 2.2 | 2.2 | 2.2 | 2.2 | 2.2 |
| Titanium oxide | 11 | 11 | 11 | 11 | 11 | 11 | 11 | 11 | 11 |
| Talc | 5 | 5 | 5 | 5 | 5 | 5 | 5 | 5 | 5 |
| Mica | 9 | 9 | 9 | 9 | 9 | 9 | 9 | 9 | 9 |
| Silica | 4 | 4 | 4 | 4 | 4 | 4 | 4 | 4 | 4 |
| Sensation at the time of application | ◎ | ◎ | ◎ | ◎ | ◎ | ◎ | ◎ | ○ | X |
| Viscosity change over time | ◎ | ◎ | ◎ | ◎ | ◎ | ◎ | ◎ | X | ◎ |
| Comprehensive rating | ◎ | ◎ | ◎ | ◎ | ◎ | ◎ | ◎ | Δ | Δ |

Table 15, 16, and 17 show Examples of a 3 component bleach containing the thickeners prepared in Synthesis examples 1-5.

The bleaches containing the thickeners of Synthesis examples 1-5 provide a stable thickening effect, give a superior sensation during use and superior external appearance.

TABLE 15

| | Example 86 | Example 86 | Example 86 | Example 86 | Example 86 |
|---|---|---|---|---|---|
| Isopropanol | 20 | 20 | 20 | 20 | 20 |
| Propylene glycol | 5 | 5 | 5 | 5 | 5 |
| POE (5) octylphenyl ether | 1 | 1 | 1 | 1 | 1 |
| Isostearic acid | 2 | 2 | 2 | 2 | 2 |
| POE (2) oleyl ether | 1 | 1 | 1 | 1 | 1 |
| POE (3) lauryl sulfate | 1 | 1 | 1 | 1 | 1 |
| Aqueous ammonia (28%) | 6 | 6 | 6 | 6 | 6 |
| Monoethanolamine | 0.6 | 0.6 | 0.6 | 0.6 | 0.6 |

TABLE 15-continued

|  | Example 86 | Example 86 | Example 86 | Example 86 | Example 86 |
|---|---|---|---|---|---|
| Hydrolyzed keratin | 1 | 1 | 1 | 1 | 1 |
| Synthesis example 1 | 0.5 | | | | |
| Synthesis example 2 | | 0.5 | | | |
| Synthesis example 3 | | | 0.5 | | |
| Synthesis example 4 | | | | 0.5 | |
| Synthesis example 5 | | | | | 0.5 |
| EDTA | Appropriate amount | Appropriate amount | Appropriate amount | Appropriate amount | Appropriate amount |
| Purified water | Balance | Balance | Balance | Balance | Balance |

TABLE 16

|  | Example 91 | Example 92 | Example 93 | Example 94 | Example 95 |
|---|---|---|---|---|---|
| Hydrogen peroxide (30%) | 20 | 20 | 20 | 20 | 20 |
| Synthesis example 1 | 1.5 | | | | |
| Synthesis example 2 | | 1.5 | | | |
| Synthesis example 3 | | | 1.5 | | |
| Synthesis example 4 | | | | 1.5 | |
| Synthesis example 5 | | | | | 1.5 |
| Sodium stannate | Appropriate amount | Appropriate amount | Appropriate amount | Appropriate amount | Appropriate amount |
| Methylparaben | Appropriate amount | Appropriate amount | Appropriate amount | Appropriate amount | Appropriate amount |
| Phosphate buffer | Adjust to pH 3 | Adjust to pH 3 | Adjust to pH 3 | Adjust to pH 3 | Adjust to pH 3 |
| Purified water | Balance | Balance | Balance | Balance | Balance |

TABLE 17

|  | Example 96 |
|---|---|
| Sodium persulfate | 50 |
| Ammonium sulfate | 10 |
| Sodium carbonate | 20 |
| Sodium laurylsulfate | 4 |
| Carboxymethyl cellulose | 10 |
| EDTA | 1 |
| Hydrolyzed collagen | 5 |

Table 18 shows Examples of a clear liquid hair treatment containing the thickeners prepared in Synthesis examples 6-7. Since anionic polymers cannot be blended in these Examples, the polymers of Synthesis examples 1-5 are not blended in. The hair treatments containing the thickeners of Synthesis examples 6-7 can provide a beautiful gel with a clear and homogeneous external appearance.

Regarding the sensation during use, the sensory evaluation of the tactile sensation during use was performed by three specialized panelists. The evaluation rating was determined based on the following criteria.

4 points: Exceptionally superior, 3 points: superior, 2 points: Hard to say whether superior or inferior, and 1 point: Inferior.

⊚: The average rating is 3.5 or more and 4 or less; ○: The average rating is 3 or more and less than 3.5; Δ: 2 or more and less than 3; X: Less than 2.

These hair treatments give a superior sensation at the time of application and cause no stickiness, resulting in a superior comprehensive rating.

TABLE 18

|  | Example 97 | Example 98 | Comparative example 21 |
|---|---|---|---|
| Polyoxyethylene/methylpolysiloxane copolymer | 6 | 6 | 6 |
| Ethanol | 10 | 10 | 10 |
| Octyldodecanol | 0.15 | 0.15 | 0.15 |
| Glycerin | 5 | 5 | 5 |
| 1.3-butylene glycol | 2 | 2 | 2 |
| Squalane | 0.1 | 0.1 | 0.1 |
| Glyceryl pyroglutamate oleate | 0.05 | 0.05 | 0.05 |
| Stearyltrimethylammonium chloride (80%) | 1.15 | 1.15 | 1.15 |
| Hydrolyzed keratin solution | 0.1 | 0.1 | 0.1 |
| N-(2-hydroxy-3-(trimethylammonio)propyl) hydrolyzed collagen chloride | 0.5 | 0.5 | 0.5 |
| Paraoxy benzoate | Appropriate amount | Appropriate amount | Appropriate amount |
| Hydroxyethylcellulose | 1 | 1 | 1 |
| Purified water | Balance | Balance | Balance |
| Synthesis example 6 | 1 | | |
| Synthesis example 7 | | 1 | |
| Xanthan gum | | | 1 |
| Perfume | Appropriate amount | Appropriate amount | Appropriate amount |
| Sensation at the time of application | ⊚ | ⊚ | Δ |
| Stickiness when it is almost dry | ⊚ | ⊚ | X |
| Comprehensive rating | ⊚ | ⊚ | X |

Table 19 shows Examples of a deodorant lotion containing the thickeners prepared in Synthesis examples 6-7. Since anionic polymers cannot be blended in these Examples, the polymers of Synthesis examples 1-5 are not blended in. The deodorant lotions containing the thickeners of Synthesis examples 6-7 can provide a beautiful gel with a clear and homogeneous external appearance.

Regarding the sensation during use, the sensory evaluation of the tactile sensation during use was performed by three specialized panelists. The evaluation rating was determined based on the following criteria.

4 points: Exceptionally superior, 3 points: superior, 2 points: Hard to say whether superior or inferior, and 1 point: Inferior.
◎: The average rating is 3.5 or more and 4 or less; ○: The average rating is 3 or more and less than 3.5; Δ: 2 or more and less than 3; X: Less than 2.

These deodorants give a superior sensation at the time of application and cause no stickiness, resulting in a superior comprehensive rating.

TABLE 19

|  | Example 99 | Example 100 | Comparative example 22 | Comparative example 23 |
|---|---|---|---|---|
| Aluminum chlorohydrate | 10 | 10 | 10 | 10 |
| Anhydrous ethyl alcohol | 60 | 60 | 60 | 60 |
| Ion-exchanged water | Balance | Balance | Balance | Balance |
| 1,3-butylene glycol | 3 | 3 | 3 | 3 |
| Benzalkonium chloride | 0.2 | 0.2 | 0.2 | 0.2 |
| Polyoxyethylene (40) hydrogenated castor oil | 0.5 | 0.5 | 0.5 | 0.5 |
| Synthesis example 6 | 1 | | | |
| Synthesis example 7 | | 1 | | |
| Hydroxyethylcellulose | | | 1 | |
| Xanthan gum | | | | 1 |
| Perfume | Appropriate amount | Appropriate amount | Appropriate amount | Appropriate amount |
| Sensation at the time of application | ◎ | ◎ | Δ | Δ |
| Stickiness | ◎ | ◎ | Δ | X |
| Comprehensive rating | ◎ | ◎ | Δ | Δ |

Table 20 shows Examples of a facial pack containing the thickeners prepared in Synthesis examples 1-5.

Since anionic polymers cannot be blended in these Examples, the polymers of Synthesis examples 6 and 7 are not blended in.

The facial packs containing the thickeners of Synthesis examples 1-5 are not sticky and give a refreshing sensation during use compared with Comparative examples.

TABLE 20

|  | Example 101 | Example 102 | Example 103 | Example 104 | Example 105 |
|---|---|---|---|---|---|
| Ethanol | 3 | 3 | 3 | 3 | 3 |
| Glycerin | 5 | 5 | 5 | 5 | 5 |
| 1,3-butylene glycol | 6 | 6 | 6 | 6 | 6 |
| Polyethylene glycol 1500 | 5 | 5 | 5 | 5 | 5 |
| Polyoxyethylene methylglycoside | 2 | 2 | 2 | 2 | 2 |
| Glyceryl tri-2-ethylhexanoate | 1 | 1 | 1 | 1 | 1 |
| Sodium hexamethaphosphate | 0.05 | 0.05 | 0.05 | 0.05 | 0.05 |
| Hydroxypropyl-β-cyclodextrin | 0.1 | 0.1 | 0.1 | 0.1 | 0.1 |
| Dipotassium glycyrrhizate | 0.1 | 0.1 | 0.1 | 0.1 | 0.1 |
| Loquat leaf extract | 0.1 | 0.1 | 0.1 | 0.1 | 0.1 |
| Sodium L-glutamate | 0.1 | 0.1 | 0.1 | 0.1 | 0.1 |
| Fennel extract | 0.1 | 0.1 | 0.1 | 0.1 | 0.1 |
| Witch hazel extract | 0.1 | 0.1 | 0.1 | 0.1 | 0.1 |
| *Phellodendri Cortex* extract | 0.1 | 0.1 | 0.1 | 0.1 | 0.1 |
| *Rehmannia* root extract | 0.1 | 0.1 | 0.1 | 0.1 | 0.1 |
| *Eucalyptus* oil | 0.05 | 0.05 | 0.05 | 0.05 | 0.05 |
| Dimorpholino pyridazine | 0.1 | 0.1 | 0.1 | 0.1 | 0.1 |
| Xanthan gum | 0.05 | 0.05 | 0.05 | 0.05 | 0.05 |
| Synthesis example 1 | 0.5 | | | | |
| Synthesis example 2 | | 0.5 | | | |
| Synthesis example 3 | | | 0.5 | | |
| Synthesis example 4 | | | | 0.5 | |
| Synthesis example 5 | | | | | 0.5 |
| Alkyl acrylate/methacrylate copolymer | 0.05 | 0.05 | 0.05 | 0.05 | 0.05 |
| Potassium hydroxide | 0.05 | 0.05 | 0.05 | 0.05 | 0.05 |
| Phenoxy ethanol | Appropriate amount | Appropriate amount | Appropriate amount | Appropriate amount | Appropriate amount |
| Purified water | Balance | Balance | Balance | Balance | Balance |

Table 21 shows Examples of a clear gel bactericide containing the thickeners prepared in Synthesis examples 6 and 7. Since anionic polymers cannot be blended in these Examples, the polymers of Synthesis examples 1-5 are not blended in. The bactericides containing the thickeners of Synthesis examples 6 and 7 are a beautiful gel with a clear and homogeneous external appearance.

Regarding the sensation during use, the sensory evaluation of the tactile sensation during use was performed by three specialized panelists. The evaluation rating was determined based on the following criteria.

4 points: Exceptionally superior, 3 points: superior, 2 points: Hard to say whether superior or inferior, and 1 point: Inferior.

◎: The average rating is 3.5 or more and 4 or less; ○: The average rating is 3 or more and less than 3.5; Δ: 2 or more and less than 3; X: Less than 2.

These bactericides give a superior sensation at the time of application and cause no stickiness, resulting in a superior comprehensive rating.

TABLE 21

|  | Example 106 | Example 107 | Comparative example 24 |
|---|---|---|---|
| Dynamite glycerin | 5 | 5 | 5 |
| Ethanol | 70 | 70 | 70 |
| Chlorhexidine | 0.2 | 0.2 | 0.2 |
| Benzalkonium chloride | 0.3 | 0.3 | 0.3 |
| Synthesis example 6 | 0.5 | | |
| Synthesis example 7 | | 0.5 | |
| Xanthan gum | | | 0.5 |
| Ion-exchanged water | Balance | Balance | Balance |
| Sensation at the time of application | ◎ | ◎ | Δ |
| Stickiness | ◎ | ◎ | X |
| Comprehensive rating | ◎ | ◎ | Δ |

Table 22 shows Examples of a body soap containing the thickeners prepared in Synthesis examples 1-5. Since anionic polymers cannot be blended in these Examples, the polymers of Synthesis examples 6 and 7 are not blended in. The body soaps containing the thickeners of Synthesis examples 1-5 do not inhibit foaming and provide a creamy foam.

TABLE 22

|  | Example 108 | Example 109 | Example 110 | Example 111 | Example 112 |
|---|---|---|---|---|---|
| Ethanol | 10 | 10 | 10 | 10 | 10 |
| Glycerin | 1 | 1 | 1 | 1 | 1 |
| Orange oil | 0.05 | 0.05 | 0.05 | 0.05 | 0.05 |
| Rosemary oil | 0.5 | 0.5 | 0.5 | 0.5 | 0.5 |
| Polyoxyethylene stearyl ether | 10 | 10 | 10 | 10 | 10 |
| Acyl cocoate/potassium glutamate mixed solution | 5 | 5 | 5 | 5 | 5 |
| Sodium methyl cocoyl taurate | 1.5 | 1.5 | 1.5 | 1.5 | 1.5 |
| 2-alkyl-N-carboxymethyl-N-hydroxyethylimidazolium betaine | 1.5 | 1.5 | 1.5 | 1.5 | 1.5 |
| Sodium hyaluronate | 0.05 | 0.05 | 0.05 | 0.05 | 0.05 |
| Citric acid | 0.1 | 0.1 | 0.1 | 0.1 | 0.1 |
| Sodium citrate | 0.2 | 0.2 | 0.2 | 0.2 | 0.2 |
| Dipotassium glycyrrhizate | 0.1 | 0.1 | 0.1 | 0.1 | 0.1 |
| Trisodium ethylenediaminehydroxyethyl triacetate | Appropriate amount | Appropriate amount | Appropriate amount | Appropriate amount | Appropriate amount |
| Synthesis example 1 | 0.5 | | | | |
| Synthesis example 2 | | 0.5 | | | |
| Synthesis example 3 | | | 0.5 | | |
| Synthesis example 4 | | | | 0.5 | |
| Synthesis example 5 | | | | | 0.5 |
| Purified water | Balance | Balance | Balance | Balance | Balance |

Table 23 shows Examples of a face washing foam containing the thickeners prepared in Synthesis examples 1-5. Since anionic polymers cannot be blended in these Examples, the polymers of Synthesis examples 6 and 7 are not blended in. The body soaps containing the thickeners of Synthesis examples 1-5 do not inhibit foaming and provide a creamy foam.

TABLE 23

|  | Example 113 | Example 114 | Example 115 | Example 116 | Example 117 |
|---|---|---|---|---|---|
| Glycerin | 6 | 6 | 6 | 6 | 6 |
| 1,3-butylene glycol | 4 | 4 | 4 | 4 | 4 |
| Polyethylene glycol 400 | 13 | 13 | 13 | 13 | 13 |
| White beeswax | 0.5 | 0.5 | 0.5 | 0.5 | 0.5 |
| Stearic acid | 20 | 20 | 20 | 20 | 20 |
| Lauric acid | 5 | 5 | 5 | 5 | 5 |
| Myristic acid | 10 | 10 | 10 | 10 | 10 |
| Polyoxyethylene (25) polyoxypropylene glycol (30) | 0.5 | 0.5 | 0.5 | 0.5 | 0.5 |

TABLE 23-continued

|  | Example 113 | Example 114 | Example 115 | Example 116 | Example 117 |
| --- | --- | --- | --- | --- | --- |
| Self-emulsified glycerin monostearate | 2 | 2 | 2 | 2 | 2 |
| Titanium oxide | 0.2 | 0.2 | 0.2 | 0.2 | 0.2 |
| Sodium citrate | 0.05 | 0.05 | 0.05 | 0.05 | 0.05 |
| Potassium hydroxide | 6.5 | 6.5 | 6.5 | 6.5 | 6.5 |
| Chamomilla extract | 0.1 | 0.1 | 0.1 | 0.1 | 0.1 |
| Trisodium edetate | Appropriate amount | Appropriate amount | Appropriate amount | Appropriate amount | Appropriate amount |
| Synthesis example 1 | 0.5 | | | | |
| Synthesis example 2 | | 0.5 | | | |
| Synthesis example 3 | | | 0.5 | | |
| Synthesis example 4 | | | | 0.5 | |
| Synthesis example 5 | | | | | 0.5 |
| Purified water | Balance | Balance | Balance | Balance | Balance |
| Perfume | Appropriate amount | Appropriate amount | Appropriate amount | Appropriate amount | Appropriate amount |

Tables 24 and 25 show Examples of a fragrance containing the thickeners prepared in Synthesis examples 1-5. The fragrances containing the thickeners of Synthesis examples 1-5 have a high concentration of ethanol; their external appearance is homogeneous and clear and they allow stable thickening.

TABLE 24

|  | Example 118 | Example 119 | Example 120 | Example 121 | Example 122 |
| --- | --- | --- | --- | --- | --- |
| Alcohol | 40 | 40 | 40 | 40 | 40 |
| Glycerin | 1 | 1 | 1 | 1 | 1 |
| PPG-13 decyltetradeceth-24 | 1 | 1 | 1 | 1 | 1 |
| t-butylmethoxy-dibenzoylmethane | 0.5 | 0.5 | 0.5 | 0.5 | 0.5 |
| 1,3-butylene glycol | 1 | 1 | 1 | 1 | 1 |
| Dipropylene glycol | 1 | 1 | 1 | 1 | 1 |
| Synthesis example 1 | 0.6 | | | | |
| Synthesis example 2 | | 0.6 | | | |
| Synthesis example 3 | | | 0.6 | | |
| Synthesis example 4 | | | | 0.6 | |
| Synthesis example 5 | | | | | 0.6 |
| Dimorpholino pyridazine | 0.1 | 0.1 | 0.1 | 0.1 | 0.1 |
| Pearl agent | 1 | 1 | 1 | 1 | 1 |
| Edetate | Appropriate amount | Appropriate amount | Appropriate amount | Appropriate amount | Appropriate amount |
| Water | Balance | Balance | Balance | Balance | Balance |
| Perfume | 1 | 1 | 1 | 1 | 1 |

TABLE 25

|  | Example 123 | Example 124 | Example 125 | Example 126 | Example 127 |
| --- | --- | --- | --- | --- | --- |
| Alcohol | 75 | 75 | 75 | 75 | 75 |
| t-butylmethoxy-dibenzoylmethane | 0.5 | 0.5 | 0.5 | 0.5 | 0.5 |
| 1,3-butylene glycol | 2 | 2 | 2 | 2 | 2 |
| Dipropylene glycol | 2 | 2 | 2 | 2 | 2 |
| Synthesis example 1 | 0.6 | | | | |
| Synthesis example 2 | | 0.6 | | | |
| Synthesis example 3 | | | 0.6 | | |
| Synthesis example 4 | | | | 0.6 | |
| Synthesis example 5 | | | | | 0.6 |
| Octyl methoxycinnamate | 5 | 5 | 5 | 5 | 5 |
| Dibutylhydroxytoluene | 0.1 | 0.1 | 0.1 | 0.1 | 0.1 |
| Perfume | 10 | 10 | 10 | 10 | 10 |
| Water | Balance | Balance | Balance | Balance | Balance |

Table 26 shows Examples of a fungicide containing the thickeners prepared in Synthesis examples 1-7. Stable gel base agents that are easy to apply can be obtained.

TABLE 26

|  | Example 128 | Example 129 | Example 130 | Example 131 | Example 132 |
|---|---|---|---|---|---|
| Sodium hypochlorite | 3 | 3 | 3 | 3 | 3 |
| Sodium hydroxide | 1 | 1 | 1 | 1 | 1 |
| Sodium cocoate | 0.5 | 0.5 | 0.5 | 0.5 | 0.5 |
| Catalyst | Appropriate amount | Appropriate amount | Appropriate amount | Appropriate amount | Appropriate amount |
| Synthesis example 1 | 1 | | | | |
| Synthesis example 2 | | 1 | | | |
| Synthesis example 3 | | | 1 | | |
| Synthesis example 4 | | | | 1 | |
| Synthesis example 5 | | | | | 1 |
| Ion-exchanged water | Balance | Balance | Balance | Balance | Balance |

Invention of Claims 15-21

Example 133

40 g of dimethylacrylamide (from Kohjin) and 9 g of 2-acrylamido-2-methylpropanesulfonic acid (from Sigma) are dissolved in 250 g of ion-exchanged water and the pH is adjusted to 7.0 with sodium hydroxide. 250 g of n-hexane, 8.2 g of polyoxyethylene (3) oleyl ether (EMALEX 503 from Nihon Emulsion), and 16.4 g of polyoxyethylene (6) oleyl ether (EMALEX 506 from Nihon Emulsion) are put into a 1,000 mL four-neck flask equipped with a refluxing apparatus, mixed and dissolved, followed by $N_2$ substitution. The monomer aqueous solution is added to this four-neck flask, and the temperature is gradually raised to 65° C.-70° C. using an oil bath as stirring is carried out in an $N_2$ atmosphere.

This polymerization system composition is monitored for the electric conductivity with a circuit tester; the phase transition temperature is determined as the temperature at which the electrical conductivity suddenly drops practically to zero (59° C.); the polymerization temperature is set to 65° C. to maintain the temperature no more than 20° C. higher than this phase transition temperature.

After confirming that the polymerization system composition has become semitransparent, 0.2 g of ammonium persulfate is added to the polymerization system composition to start the polymerization. The polymerization system is stirred and kept at the aforementioned temperature for four hours to obtain the water-swelling polymer.

After the polymerization, a large amount of acetone is added to the microgel suspension to precipitate the microgel, followed by rinsing with acetone three times to remove the remaining monomers and the surfactant. The precipitate was filtered and then dried under a reduced pressure to obtain a dried water-swelling polymer in a white powder form. The yield was 96%. The obtained water-swelling polymer was dispersed in ion-exchanged water to have a concentration of 0.5% and the apparent viscosity and the dynamic elastic modulus were measured.

Figure 7:
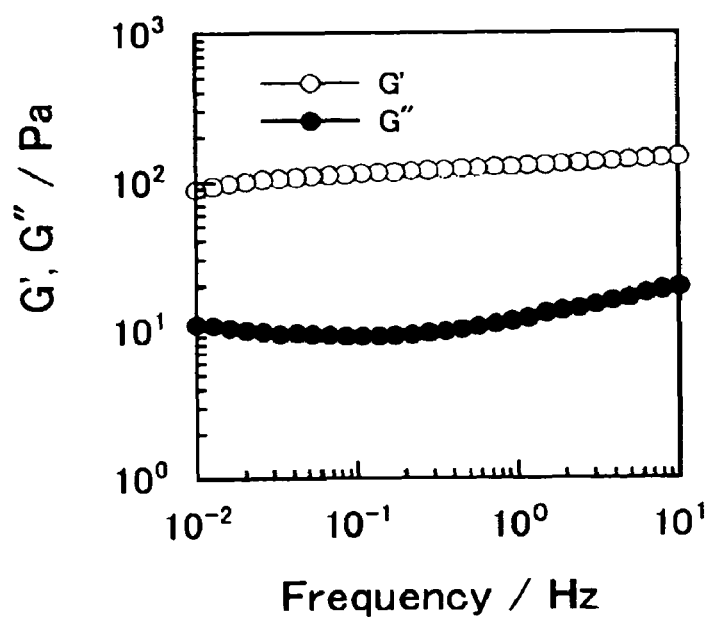
FIG. 7 is a graph showing the dynamic elastic modulus of the water-swelling polymer obtained in Example 1 dispersed in water.

The results for the apparent viscosity, the phase transition temperature, and the polymerization temperature are shown in Table 27, and the results for the dynamic elastic modulus are shown in FIG. 7.

Example 134

35 g of dimethylacrylamide (from Kohjin) and 17.5 g of 2-acrylamido-2-methylpropanesulfonic acid (from Sigma) are dissolved in 250 g of ion-exchanged water and the pH is adjusted to 7.0 with sodium hydroxide. 250 g of n-hexane, 8.2 g of polyoxyethylene (3) oleyl ether (EMALEX 503 from Nihon Emulsion), and 16.4 g of polyoxyethylene (6) oleyl ether (EMALEX 506 from Nihon Emulsion) are put into a 1,000 mL four-neck flask equipped with a refluxing apparatus, mixed and dissolved, followed by $N_2$ substitution. The monomer aqueous solution is added to this four-neck flask, and the temperature is gradually raised to 65° C.-70° C. using an oil bath as stirring is carried out in an $N_2$ atmosphere.

This polymerization system composition is monitored for the electric conductivity with a circuit tester; the phase transition temperature is determined as the temperature at which the electrical conductivity suddenly drops practically to zero (60° C.); the polymerization temperature is set to 65° C. to maintain the temperature no more than 20° C. higher than this phase transition temperature.

After confirming that the polymerization system composition has become semitransparent, 0.2 g of ammonium persulfate is added to the polymerization system composition to start the polymerization. The polymerization system is stirred and kept at the aforementioned temperature for four hours to obtain the water-swelling polymer.

After the polymerization, a large amount of acetone is added to the microgel suspension to precipitate the microgel, followed by rinsing with acetone three times to remove the remaining monomers and the surfactant. The precipitate was filtered and then dried under a reduce pressure to obtain a dried water-swelling polymer in a white powder form. The yield was 95%. The obtained water-swelling polymer was dispersed in ion-exchanged water to have a concentration of 0.5% and the apparent viscosity and the dynamic elastic modulus were measured.

Figure 8:
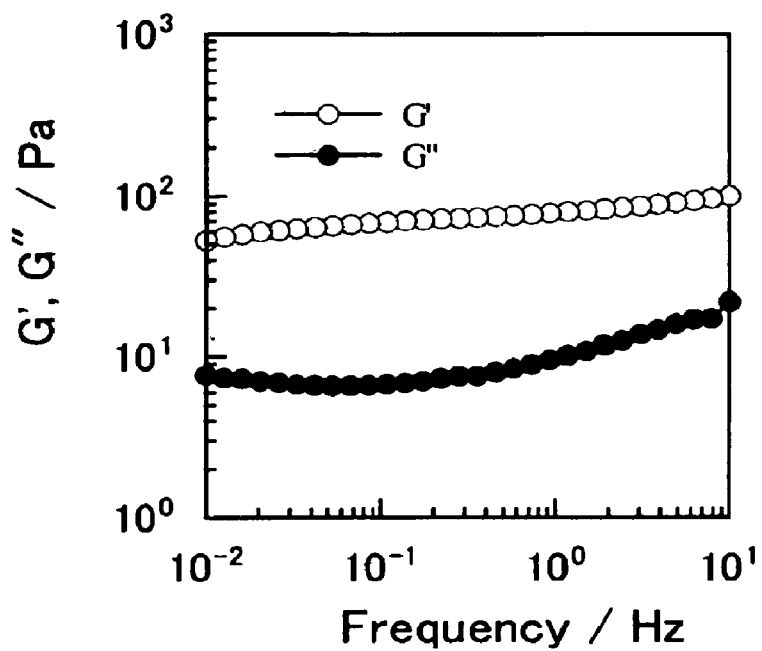
FIG. 8 is a graph showing the dynamic elastic modulus of the water-swelling polymer obtained in Example 2 dispersed in water.

The results for the apparent viscosity, the phase transition temperature, and the polymerization temperature are shown in Table 27, and the results for the dynamic elastic modulus are shown in FIG. 8.

Example 135

30 g of dimethylacrylamide (from Kohjin) and 26.7 g of 2-acrylamido-2-methylpropanesulfonic acid (from Sigma) are dissolved in 250 g of ion-exchanged water and the pH is adjusted to 7.0 with sodium hydroxide. 250 g of n-hexane, 8.2 g of polyoxyethylene (3) oleyl ether (EMALEX 503 from Nihon Emulsion), and 16.4 g of polyoxyethylene (6) oleyl ether (EMALEX 506 from Nihon Emulsion) are put into a 1,000 mL four-neck flask equipped with a refluxing apparatus, mixed and dissolved, followed by $N_2$ substitution. The monomer aqueous solution is added to this four-neck flask, and the temperature is gradually raised to 65° C.-70° C. using an oil bath as stirring is carried out in an $N_2$ atmosphere.

This polymerization system composition is monitored for the electric conductivity with a circuit tester; the phase transition temperature is determined as the temperature at which the electrical conductivity suddenly drops practically to zero (55° C.); the polymerization temperature is set to 68° C. to maintain the temperature no more than 20° C. higher than this phase transition temperature.

After confirming that the polymerization system composition has become semitransparent, 0.2 g of ammonium persulfate is added to the polymerization system composition to start the polymerization. The polymerization system is stirred and kept at the aforementioned temperature for four hours to obtain the water-swelling polymer.

After the polymerization, a large amount of acetone is added to the microgel suspension to precipitate the microgel, followed by rinsing with acetone three times to remove the remaining monomers and the surfactant. The precipitate was filtered and then dried under a reduced pressure to obtain a dried water-swelling polymer in a white powder form. The yield was 95%. The obtained water-swelling polymer was dispersed in ion-exchanged water to have a concentration of 0.5% and the apparent viscosity and the dynamic elastic modulus were measured.

Figure 9:
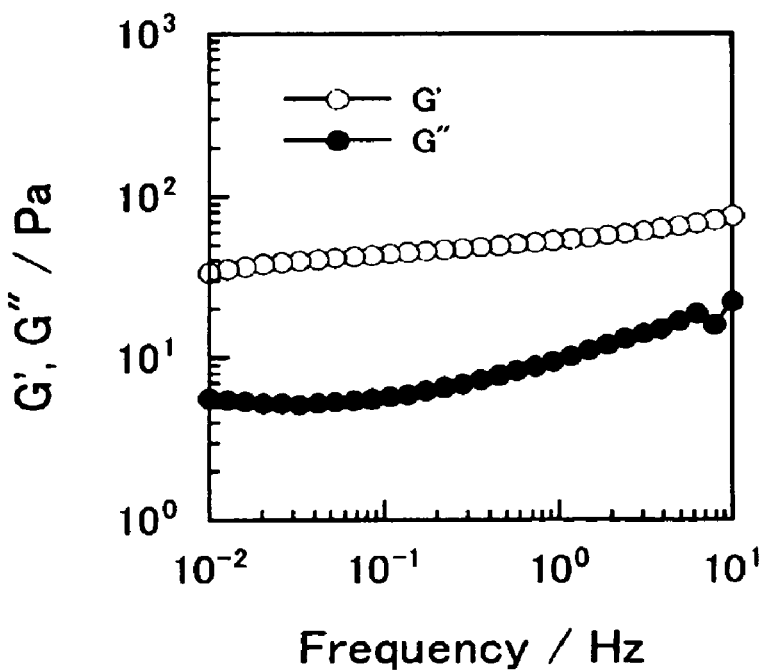
FIG. 9 is a graph showing the dynamic elastic modulus of the water-swelling polymer obtained in Example 3 dispersed in water.

The results for the apparent viscosity, the phase transition temperature, and the polymerization temperature are shown in Table 27, and the results for the dynamic elastic modulus are shown in FIG. 9.

Comparative Example 25

Polymerization Performed Outside of the A Region 35 g of dimethylacrylamide (from Kohjin) and 17.5 g of 2-acrylamido-2-methylpropanesulfonic acid (from Sigma) are dissolved in 250 g of ion-exchanged water and the pH is adjusted to 7.0 with sodium hydroxide. 250 g of n-hexane, 16.4 g of polyoxyethylene (3) oleyl ether (EMALEX 503 from Nihon Emulsion), and 8.2 g of polyoxyethylene (6) oleyl ether (EMALEX 506 from Nihon Emulsion) are put into a 1,000 mL four-neck flask equipped with a refluxing apparatus, mixed and dissolved, followed by $N_2$ substitution. The monomer aqueous solution is added to this four-neck flask, and the temperature is gradually raised to 65° C.-70° C. using an oil bath as stirring is carried out in an $N_2$ atmosphere.

This polymerization system composition is monitored for the electric conductivity with a circuit tester; the phase transition temperature is determined as the temperature at which the electrical conductivity suddenly drops practically to zero (23° C.); the polymerization temperature is set to 66° C. to maintain the temperature more than 20° C. higher than this phase transition temperature.

0.2 g of ammonium persulfate is then added to the polymerization system to start the polymerization. The polymerization system is stirred and kept at the aforementioned temperature for four hours to obtain the water-swelling polymer.

After the polymerization, a large amount of acetone is added to the microgel suspension to precipitate the microgel, followed by rinsing with acetone three times to remove the remaining monomers and the surfactant. The precipitate was filtered and then dried under a reduced pressure to obtain a dried water-swelling polymer in a white powder form. The yield was 96%. The obtained water-swelling polymer was dispersed in ion-exchanged water to have a concentration of 0.5% and the apparent viscosity was measured.

The results for the measurements of the apparent viscosity, the phase transition temperature, and the polymerization temperature are shown in Table 27.

TABLE 27

|  | Example 133 | Example 134 | Example 135 | Comparative example 25 |
|---|---|---|---|---|
| Viscosity (1) | 28400 | 30700 | 31000 | 2300 |
| Phase transition temperature (2) | 59° C. | 60° C. | 55° C. | 23° C. |
| Thermal radical aforementioned temperature (3) | 65° C. | 65° C. | 68° C. | 66° C. |

(1) The apparent viscosity (mPa · s) of a 0.5% ion-exchanged water dispersion at a shear rate of 1.0 s$^{-1}$
(2) The temperature at which the electric conductivity changed to zero.
(3) The average temperature of the polymerization system composition during the polymerization

INDUSTRIAL APPLICABILITY

The thickener of the present invention exhibits a superior thickening effect when blended in cosmetics. Sliminess at the time of application of the cosmetic and stickiness when it is almost dry, which have been problematic for conventional thickeners, are greatly reduced and cosmetics that give an exceptionally superior sensation during use can be manufactured.

In the manufacturing method of the thickener of the present invention, the polymerized microgel can be isolated in a powder form and used as a thickener. Therefore, no crushing is necessary as in the case of a conventional polymer gel. The microgel thus isolated in a powder form is easily dispersed in water, ethanol, or a water/ethanol mixed solvent and quickly swells and functions as an excellent thickener. Also, by choosing a strongly acidic monomer (a monomer containing a sulfonic acid residue, for example) for the water soluble ethylene type unsaturated monomer to be copolymerized into the microgel, even an acidic formulation can be thickened, which was not possible with conventional carboxyvinyl polymers.

Furthermore, the thickener of the present invention can thicken or gel alcohol, which conventionally was difficult.

By using the manufacturing method of the present invention, a water-swelling polymer with a superior thickening effect can be manufactured.

The water-swelling polymer obtained from the radical polymerization according to the manufacturing method of the present invention takes the form of a powdery microgel; when used as a thickener it has the advantage of not requiring crushing as polymer gel obtained from a conventional manufacturing method would require.

The invention claimed is:
1. A method of thickening a cosmetic comprising adding thereto a microgel, said microgel being produced via radical reverse phase emulsion polymerization of a mixture of water soluble monomers of a dialkylacrylamide represented by general formula (1) and an anionic acrylamide derivative represented by general formula (2) as follows:

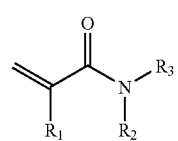

General formula (1)

wherein R1 denotes a H or methyl group; R2 and R3, independent of each other, denote a methyl, ethyl, propyl, or isopropyl group;

General formula (2)

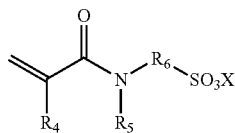

wherein R4 and R5, independent of each other, denote a H or methyl group, R6 denotes a straight chain or branched alkyl group having 1-6 carbon atoms, and X denotes a metal ion or NH3;

dissolved in a dispersion phase in a polymerization system composition having an organic solvent or an oil component as the dispersion medium and water as the dispersion phase, wherein said polymerization system composition contains a surfactant and forms a single phase microemulsion or fine W/O emulsion said polymerization being carried out in a thermodynamically stable single microemulsion region or a metastable fine W/O emulsion region of a phase diagram for the polymerization system composition, wherein said microgel has:
(a) an apparent viscosity of a microgel aqueous dispersion (0.5% mass percentage of the microgel at 25° C.) of 10,000 mPa·s or higher at a shear rate of $1.0\ s^{-1}$;
(b) an apparent viscosity of a microgel ethanol dispersion (0.5% mass percentage of the microgel at 25° C.) of 5,000 mPa·s or higher at a shear rate of $1.0\ s^{-1}$; and
(c) a dynamic elastic modulus of a microgel aqueous or ethanol dispersion having 0.5% (mass percentage) at 25° C. satisfying a relationship G' (stored elastic modulus) greater than G" (loss elastic modulus) at a strain of 1% or less and a frequency range of 0.01-10 Hz.

2. The method of thickening a cosmetic of claim 1, wherein the microgel is in powder form.

3. The method of thickening cosmetics of claim 1, wherein the powder microgel is first dispersed in water, ethanol, or a water/ethanol mixed solvent to form a thickener, and the thickener is then added to the cosmetic.

4. The method of thickening a cosmetic of claim 1, wherein 0.1-10 mass % of the microgel is added to the cosmetic.

5. The method of thickening a cosmetic of claim 1, wherein said microgel exhibits a stable thickening effect over a pH range of about 2 to about 11.

6. The method of thickening a cosmetic of claim 1, wherein an organic solvent and surfactant in the polymerization system composition are selected so a single phase microemulsion for fine W/O emulsion region in the phase diagram corresponds to an optimum polymerization temperature for a polymerization initiator for a thermal polymerization or redox polymerization.

7. The method of thickening a cosmetic of claim 1, wherein the polymerization system composition contains a surfactant chosen so that the polymerization system composition has a clouding point at a temperature used for thermal radical polymerization.

8. The method of thickening a cosmetic of claim 1, comprising radical polymerization of water soluble ethylene-type unsaturated monomers dissolved in the dispersion phase in a composition having an organic solvent or an oil component as the dispersion medium and water as the dispersion phase.

9. A method of thickening a cosmetic comprising adding thereto a microgel, said microgel being produced via radical polymerization of a mixture of water soluble monomers of:

a dialkylacrylamide represented by general formula (1),
an anionic acrylamide derivative represented by general formula (2) and
a cross-linking monomer represented by general formula (4) as follows:

General formula (1)

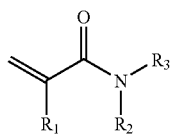

($R_1$ denotes a H or methyl group; $R_2$ and $R_3$, independent of each other, denote a methyl, ethyl, propyl, or isopropyl group);

General formula (2)

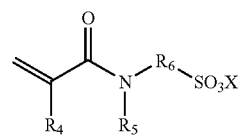

($R_4$ and $R_5$, independent of each other, denote a H or methyl group, $R_6$ denotes a straight chain or branched alkyl group having 1-6 carbon atoms, and X denotes a metal ion or $NH_3$);

General formula (4)

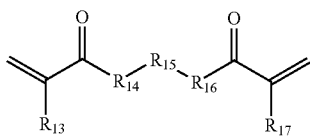

$\{$ $R_{13}$ and $R_{17}$ denote a H or methyl group;
$R_{14}$ and $R_{16}$ denote —O— or —N(H)— ;

$R_{15}$ denotes a straight chain or branched alkyl group having 1-6 carbon atoms or —(CH$_2$CH$_2$O)$_n$—

(n = 4-100).

dissolved in a dispersion phase in a polymerization system composition having an organic solvent or an oil component as the dispersion medium and water as the dispersion phase, wherein said polymerization system composition contains a surfactant and forms a single phase microemulsion or fine W/O emulsion said polymerization being carried out in a thermodynamically stable single microemulsion region or a metastable fine W/O emulsion region of a phase diagram for the polymerization system composition, and wherein said microgel has (a) an apparent viscosity of a microgel aqueous dispersion (0.5% mass percentage of the microgel at 25° C.) of 10,000 mPa·s or higher at a shear rate of 1.0 s−1; (b) an apparent viscosity of a microgel ethanol dispersion (0.5% mass percentage of the microgel at 25° C.) of 5,000 mPa·s or higher at a shear rate of 1.0 s−1; and (c) a dynamic elastic modulus of a microgel aqueous or ethanol dispersion having 0.5% (mass percentage) at 25° C. satisfying a relationship G' (stored elastic modulus) greater than G" (loss elastic modulus) at a strain of 1% or less and a frequency range of 0.01-10 Hz.

10. The method of thickening a cosmetic of claim 9, wherein the microgel is in powder form.

11. The method of thickening cosmetics of claim 9, wherein the powder microgel is first dispersed in water, ethanol, or a water/ethanol mixed solvent to form a thickener, and the thickener is then added to the cosmetic.

12. The method of thickening a cosmetic of claim 9, wherein 0.1-10 mass % of the microgel is added to the cosmetic.

13. The method of thickening a cosmetic of claim 9, wherein said microgel exhibits a stable thickening effect over a pH range of about 2 to about 11.

14. The method of thickening a cosmetic of claim 9, wherein an organic solvent and surfactant in the polymerization system composition are selected so a single phase microemulsion for fine W/O emulsion region in the phase diagram corresponds to an optimum polymerization temperature for a polymerization initiator for a thermal polymerization or redox polymerization.

15. The method of thickening a cosmetic of claim 9, wherein the polymerization system composition contains a surfactant chosen so that the polymerization system composition has a clouding point at a temperature used for thermal radical polymerization.

16. The method of thickening a cosmetic of claim 9, comprising radical polymerization of water soluble ethylene-type unsaturated monomers dissolved in the dispersion phase in a composition having an organic solvent or an oil component as the dispersion medium and water as the dispersion phase.

* * * * *